United States Patent
Thomas et al.

(10) Patent No.: US 6,700,036 B2
(45) Date of Patent: *Mar. 2, 2004

(54) ACQUISITION DISTRIBUTION LAYER HAVING VOID VOLUMES FOR AN ABSORBENT ARTICLE

(75) Inventors: Paul Eugene Thomas, Terre Haute, IN (US); Thomas Patrick Marsh, Clinton, IN (US)

(73) Assignee: Tredegar Film Products Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/823,538

(22) Filed: Mar. 30, 2001

(65) Prior Publication Data

US 2002/0062113 A1 May 23, 2002

Related U.S. Application Data

(63) Continuation-in-part of application No. 09/668,649, filed on Sep. 22, 2000.

(51) Int. Cl.[7] .................................................. A61F 13/15
(52) U.S. Cl. .................................. 604/383; 604/385.01
(58) Field of Search ................................ 604/378, 383, 604/380, 379, 385.01

(56) References Cited

U.S. PATENT DOCUMENTS

| | | | | |
|---|---|---|---|---|
| 2,226,384 A | 12/1940 | Norris | ........................... | 204/11 |
| 3,054,148 A | 9/1962 | Zimmerli | ....................... | 18/56 |
| RE26,152 E | 1/1967 | Andren | ........................... | 29/33 |
| 3,644,158 A | 2/1972 | Strumbos | .................... | 156/197 |
| 3,762,415 A | 10/1973 | Morrison | .................... | 128/290 |
| 3,860,003 A | 1/1975 | Buell | ............... | 128/287 |
| 3,911,173 A | 10/1975 | Sprague, Jr. | ................ | 427/207 |

(List continued on next page.)

FOREIGN PATENT DOCUMENTS

| | | |
|---|---|---|
| DE | 1910334 A | 9/1969 |
| EP | 0 040 084 | 11/1981 |
| EP | 0788874 A | 8/1997 |
| GB | 2262906 A | 7/1993 |
| WO | 92/11830 | 7/1992 |
| WO | 95/24877 A | 9/1995 |
| WO | 97/06765 A | 12/1997 |

OTHER PUBLICATIONS

European Patent Office Standard Search Report RS 106376; Dated Jul. 6, 2001 in connection with U.S. 668649 filed Sept. 22, 2000.

James P. Hanson, *"The Test Mess Part III—Credible Testing for Liquid Acquisition"*; Nonwovens World, Fall 1997, pp 57–58, 60 and 63.

Primary Examiner—Weilun Lo
Assistant Examiner—Jamisue A Webb
(74) Attorney, Agent, or Firm—Fish & Richardson P.C.

(57) ABSTRACT

An absorbent article having a topsheet and an absorbent core material. The acquisition distribution layer is located between the topsheet and the absorbent core material. The acquisition distribution layer is made of a three dimensional apertured film that defines a large void volume space between the acquisition distribution layer and the absorbent core material. The acquisition distribution layer provides high void volume for lateral spillage during repeated insult moments because the topsheet, which is in contact with the user, is held away from dispersing fluid that is unabsorbed by saturated core material. The void volume space provides a pathway for unabsorbed fluid to flow over the top plane of saturated core regions to unsaturated regions of the core material for absorption. The void volume space allows this migration of fluid to occur without the fluid coming into contact with the topsheet, thereby avoiding a feeling of wetness for a wearer.

19 Claims, 12 Drawing Sheets

U.S. PATENT DOCUMENTS

| | | | | |
|---|---|---|---|---|
| 3,939,135 A | | 2/1976 | Hwa et al. | 260/87.1 |
| 3,945,386 A | | 3/1976 | Anczurowski et al. | 128/287 |
| 3,965,906 A | | 6/1976 | Karami | 128/287 |
| 3,967,623 A | | 7/1976 | Butterworth et al. | 128/287 |
| 3,994,299 A | | 11/1976 | Karami | 128/287 |
| 4,055,180 A | * | 10/1977 | Karami | 428/137 |
| RE29,524 E | | 1/1978 | Spencer | 428/134 |
| 4,151,240 A | | 4/1979 | Lucas et al. | 264/504 |
| 4,253,461 A | | 3/1981 | Strickland et al. | 128/287 |
| 4,285,343 A | | 8/1981 | McNair | 128/287 |
| 4,323,069 A | | 4/1982 | Ahr et al. | 128/287 |
| 4,324,246 A | * | 4/1982 | Mullane et al. | 604/366 |
| 4,324,247 A | | 4/1982 | Aziz | 128/287 |
| 4,342,314 A | | 8/1982 | Radel et al. | 128/287 |
| 4,351,784 A | | 9/1982 | Thomas et al. | 264/22 |
| 4,383,896 A | | 5/1983 | Pruyn et al. | 204/11 |
| 4,389,211 A | * | 6/1983 | Lenaghan | 604/383 |
| 4,395,215 A | | 7/1983 | Bishop | 425/290 |
| 4,397,704 A | | 8/1983 | Frick | 156/201 |
| 4,456,570 A | | 6/1984 | Thomas et al. | 264/22 |
| 4,463,045 A | | 7/1984 | Ahr et al. | 428/131 |
| 4,508,256 A | | 4/1985 | Radel et al. | 228/152 |
| 4,509,908 A | | 4/1985 | Mullane, Jr. | 425/290 |
| 4,535,020 A | | 8/1985 | Thomas et al. | 428/131 |
| 4,541,794 A | | 9/1985 | Raley et al. | 425/290 |
| 4,543,299 A | * | 9/1985 | Raley et al. | 29/523 |
| 4,573,986 A | | 3/1986 | Minetola et al. | 604/366 |
| 4,589,876 A | | 5/1986 | Van Tilburg | 604/385 |
| 4,597,760 A | | 7/1986 | Buell | 604/397 |
| 4,597,761 A | | 7/1986 | Buell | 604/397 |
| 4,609,518 A | | 9/1986 | Curro et al. | 264/504 |
| 4,610,678 A | | 9/1986 | Weisman et al. | 604/368 |
| 4,629,643 A | | 12/1986 | Curro et al. | 428/131 |
| 4,636,161 A | | 1/1987 | Raley et al. | 425/194 |
| 4,637,819 A | | 1/1987 | Ouellette et al. | 604/369 |
| 4,644,623 A | | 2/1987 | Raley et al. | 29/148.4 D |
| 4,673,402 A | | 6/1987 | Weisman et al. | 604/368 |
| 4,687,478 A | | 8/1987 | Van Tilburg | 604/387 |
| 4,695,278 A | | 9/1987 | Lawson | 604/385 |
| 4,695,422 A | | 9/1987 | Curro et al. | 264/504 |
| 4,704,115 A | | 11/1987 | Buell | 604/385 |
| 4,738,676 A | | 4/1988 | Osborn, III | 604/385 |
| 4,772,444 A | | 9/1988 | Curro et al. | 264/557 |
| 4,778,644 A | | 10/1988 | Curro et al. | 264/557 |
| 4,781,710 A | | 11/1988 | Megison et al. | 604/378 |
| 4,785,966 A | | 11/1988 | Waltke | 220/345 |
| 4,834,735 A | | 5/1989 | Alemany et al. | 604/368 |
| 4,839,216 A | | 6/1989 | Curro et al. | 428/134 |
| 4,842,666 A | | 6/1989 | Werenicz | 156/161 |
| 4,854,984 A | | 8/1989 | Ball et al. | 156/73.5 |
| 4,888,231 A | | 12/1989 | Angstadt | 428/213 |
| 4,895,749 A | | 1/1990 | Rose | 428/132 |
| 4,895,984 A | | 1/1990 | Eggersdorfer et al. | 568/319 |
| 4,909,802 A | | 3/1990 | Ahr et al. | 604/385.1 |
| 4,909,803 A | | 3/1990 | Aziz et al. | 604/385.2 |
| 4,917,697 A | | 4/1990 | Osborn, III et al. | 604/387 |
| 4,939,135 A | | 7/1990 | Robertson et al. | 514/179 |
| 4,950,264 A | | 8/1990 | Osborn, III | 604/385.1 |
| 4,964,860 A | | 10/1990 | Gipson et al. | 604/391 |
| 4,995,930 A | | 2/1991 | Merz et al. | 156/209 |
| 5,007,906 A | | 4/1991 | Osborn, III et al. | 604/385.1 |
| 5,009,653 A | | 4/1991 | Osborn, III | 604/385.1 |
| 5,173,351 A | * | 12/1992 | Ruppel et al. | 162/111 |
| 5,188,625 A | * | 2/1993 | Van Iten et al. | 604/383 |
| 5,242,435 A | * | 9/1993 | Murji et al. | 604/374 |
| 5,268,213 A | | 12/1993 | Murakami et al. | 428/163 |
| 5,300,054 A | * | 4/1994 | Feist et al. | 604/358 |
| 5,342,334 A | | 8/1994 | Thompson et al. | 604/366 |
| 5,342,338 A | | 8/1994 | Roe | 604/383 |
| 5,364,382 A | | 11/1994 | Latimer et al. | 604/378 |
| 5,382,217 A | | 1/1995 | Namowitz | 493/310 |
| 5,422,178 A | | 6/1995 | Swenson et al. | 428/343 |
| 5,478,335 A | | 12/1995 | Colbert | 604/383 |
| 5,490,846 A | | 2/1996 | Ellis et al. | 604/366 |
| 5,603,707 A | | 2/1997 | Trombetta et al. | 604/383 |
| 5,614,283 A | * | 3/1997 | Potnis et al. | 428/131 |
| 5,628,856 A | | 5/1997 | Dobrin et al. | 156/244.18 |
| 5,635,275 A | | 6/1997 | Biagioli et al. | 428/132 |
| H1670 H | | 7/1997 | Aziz et al. | 604/367 |
| 5,645,672 A | | 7/1997 | Dobrin | 156/244.18 |
| 5,648,142 A | * | 7/1997 | Phillips | 428/132 |
| 5,669,895 A | * | 9/1997 | Murakami et al. | 604/358 |
| 5,693,037 A | | 12/1997 | Lee et al. | 604/381 |
| 5,700,254 A | | 12/1997 | McDowall et al. | 604/378 |
| 5,728,446 A | | 3/1998 | Johnston et al. | 428/167 |
| 5,770,144 A | | 6/1998 | James et al. | 264/504 |
| 5,846,230 A | | 12/1998 | Osborn, III et al. | 604/378 |
| 5,876,388 A | | 3/1999 | McDowall et al. | 604/384 |
| 5,894,044 A | | 4/1999 | Norcom et al. | 428/116 |
| 5,916,462 A | | 6/1999 | James et al. | 219/121.71 |
| 5,945,196 A | * | 8/1999 | Rieker et al. | 264/154 |
| 5,997,986 A | | 12/1999 | Turi et al. | 428/138 |
| 6,022,607 A | | 2/2000 | James et al. | 428/131 |
| 6,117,523 A | | 9/2000 | Sugahara | 428/134 |

* cited by examiner

Sample 2

Sample 4

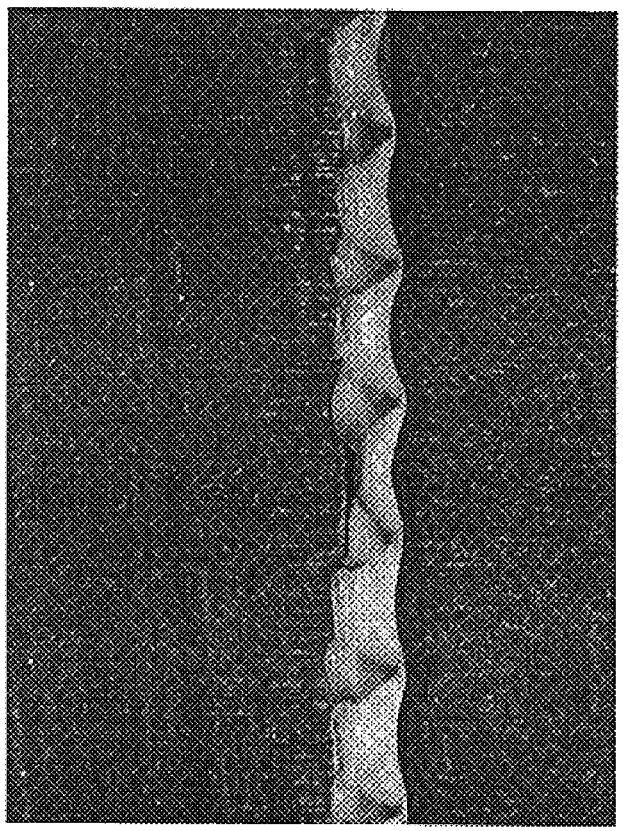
Sample 2
FIG. 20
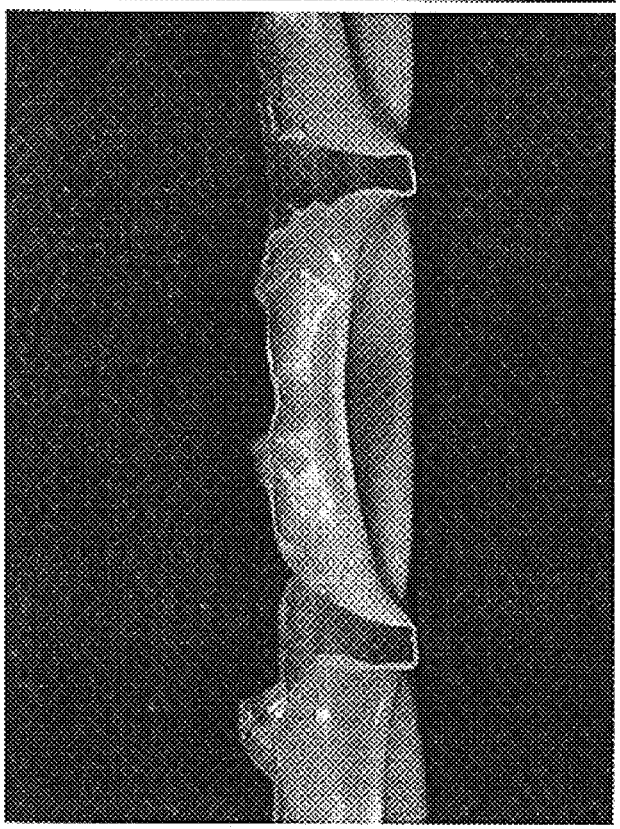
Sample 4

ACQUISITION DISTRIBUTION LAYER HAVING VOID VOLUMES FOR AN ABSORBENT ARTICLE

RELATED APPLICATIONS

This application is a continuation-in-part of U.S. Ser. No. 09/668,649 filed on Sep. 22, 2000.

FIELD OF THE INVENTION

This invention relates to absorbent articles such as diapers, incontinent articles, sanitary napkins, and the like. More particularly, this invention relates to absorbent articles having a topsheet and a film acquisition distribution layer (ADL) having a void volume space.

BACKGROUND OF THE INVENTION

A variety of absorbent articles that are adapted to absorb body fluids are well known. Examples of absorbent articles include diapers, incontinent articles, and sanitary napkins.

One problem associated with known absorbent articles is waste product leakage, which may contaminate clothing articles, such as pants, shirts, and bedding. The amount of leakage experienced by a wearer can be reduced by increasing the rate that liquid enters the absorbent core. Therefore, an absorbent article wherein liquid rapidly penetrates the topsheet and is contained in the absorbent core will experience less leakage than an absorbent article wherein liquid is able to run across the topsheet before penetrating into the absorbent core. Consequently, run-off reduction reduces the amount of leakage associated with an absorbent article.

Another problem associated with absorbent articles is dryness of the skin contacting surface of the article. Generally, the drier the skin contacting surface, the more comfortable the absorbent article. Attempts have been made to reduce surface wetness in disposable diaper structures. For example, U.S. Pat. No. 3,945,386 issued to Anczurowski on Mar.23, 1976 and U.S. Pat. Nos. 3,965,906 and 3,994,299 issued to Karami on Jun. 29, 1976 and Nov. 30, 1976, respectively, teach diaper structures having a perforated thermoplastic film interposed between the topsheet and the absorbent core. U.S. Pat. No. 4,324,247 issued to Aziz on Apr. 13, 1982 describes an effort directed to both reducing run-off and reducing the surface wetness of absorbent articles.

In addition to the dryness of the skin contacting surface, the feel of the skin contacting surface is also an important consideration. One problem is that some consumers do not like the plastic feel associated with formed films. A number of efforts have been directed at improving the feel of the surface of absorbent articles. One example is described in U.S. Pat. No. 3,967,623 issued to Butterworth, et al. The Butterworth patent teaches an absorbent pad having a facing sheet made of a perforated thermoplastic web that has an integral fibrous or sueded outer surface.

An additional problem with typical absorbent articles, in particular adult incontinence diapers. As a wearer urinates a second time or more, a sensation of wetness is felt as unabsorbed fluid flows laterally through the topsheet from an area of saturated core material to an area of unsaturated core material for absorption. This sensation is highly uncomfortable and undesirable.

The products described in most of the above references, however, are less than ideal in achieving a good combination of all three desired properties of reduced surface run-off, improved ability to prevent a feeling of wetness of the topsheet, and improved feel.

SUMMARY OF THE INVENTION

The invention relates to an absorbent article having a topsheet and an absorbent core material. An acquisition distribution layer is located between the topsheet and the absorbent core material. The acquisition distribution layer is made of a three dimensional formed film with apertures, wherein the acquisition distribution layer has a body facing side, i.e. a female side, and a garment facing side, i.e. a male side. In accordance with the invention, the acquisition distribution layer defines a high void volume space. The large under-side void volume space provides space for unabsorbed fluid to flow over the top plane of saturated core regions and flow to new, unsaturated regions of the core material without contacting the topsheet, thereby avoiding a feeling of wetness for the user. Unabsorbed fluid results from repeated insults to a saturated zone of an absorbent core. In another embodiment, the acquisition distribution layer has at least one raised ridge extending upwards to a higher plane on the female side. The raised ridge runs in the machine direction for directing unabsorbed fluid to flow primarily in the machine direction of the absorptive device to help prevent side leakage. The "machine direction" is a term of art that indicates the general direction of movement of materials during processing. Typically, if no separate tentering step is performed on the material, polymer strands within the material orient themselves generally in the machine direction of the film. In another embodiment a first and a second three dimensional apertured film forms an acquisition distribution layer having a further enlarged void volume space for flow of unabsorbed fluid and that provides a greater spacial separation between areas of containment of wetness and the topsheet. In still another embodiment, the acquisition distribution layer has a high loft, which forms relatively deep cells or buckets. When repeated insults are delivered to a saturated core region, a bucket or buckets in the insult region is filled. Subsequent insults result in fluid spilling over to adjacent buckets. The spill over action disperses the liquid volume of the insults over a larger area of the core material so that the fluid may be absorbed by unsaturated core material.

Further embodiments provide channels that are cut below a surface plane formed by the female or garment facing side of either the acquisition distribution layer having a large under-side void volume space, i.e., "spill under embodiment" or acquisition distribution layer having a high loft that forms buckets, i.e., "spill over embodiment". The channels may also be used with other embodiments. The channels provide void space for fluid flow and directs the fluid flow in desired directions. The channels provide a new spill over passage that provides a spill over volume not previously possible with a "spill under" embodiment described above. Additionally, the channels improve the volume of the spill over in the "spill over" embodiment discussed above by providing a preferred directional pathway for spilling into the next "bucket" as well as by providing more volumetric pathways to spill and redistribute the fluid.

BRIEF DESCRIPTION OF THE DRAWINGS

FIG. 20 is a cross-sectional view at 50X magnification of Sample 2 and Sample 4 for purposes of comparing the void volume space of the samples.

DETAILED DESCRIPTION OF THE INVENTION

Figure 1:
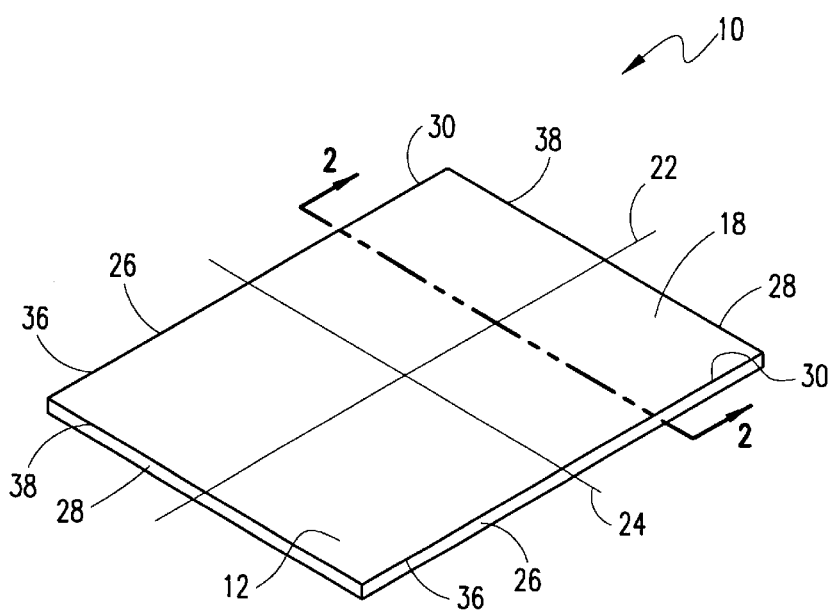
FIG. 1 is perspective view of an absorbent article of the invention that utilizes an acquisition distribution layer.

This invention relates to absorbent articles having a three dimensional apertured film acquisition distribution layer. Examples of absorbent articles include diapers, incontinent articles, sanitary napkins, and similar articles.

For purposes of this application, the term "absorbent article" will refer to articles that absorb and contain body exudates. More specifically, the term refers to articles which are placed against or in proximity to the body of a wearer for absorbing and containing various exudates discharged from the body. The term "absorbent article", as used herein, is intended to include diapers, incontinent articles, sanitary napkins, pantiliners, and other articles used to absorb body exudates.

The term "diaper" refers to a garment typically worn by infants and incontinent persons that is drawn up between the legs and fastened about the waist of the wearer. Examples of diapers from the prior art include diapers described in U.S. Pat. Re. No. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986; U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany, et al. on May 30, 1989; U.S. Pat. No. 4,888,231 issued to Angstadt on Dec. 19, 1989; and U.S. Pat. No. 4,909,803 issued to Aziz, et al. on Mar. 20, 1990.

The term "incontinent article" refers to pads, undergarments, e.g., pads held in place by a suspension system, such as a belt, or other device, inserts for absorbent articles, capacity boosters for absorbent articles, briefs, bed pads, and similar devices, whether worn by adults or other incontinent persons. Examples of incontinent articles include those disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. Nos. 4,704,115; 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991.

The term "sanitary napkin" refers to an article that is worn by a female adjacent to the pudendal region that is intended to absorb and contain various exudates which are discharged from the body, e.g., blood, menses, and urine. Examples of sanitary napkins are disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264, and 5,009,653 issued to Osborn on Aug. 21, 1990 and Apr. 23, 1991, respectively; and in U.S. patent application Ser. No. 07/605,583 filed Oct. 29, 1990 in the name of Visscher, et al.

The term "pantiliner" refers to absorbent articles that are less bulky than sanitary napkins that are generally worn by women between their menstrual periods. Examples of pantiliners are disclosed in U.S. Pat. No. 4,738,676 entitled "Pantiliner" issued to Osborn on Apr. 19, 1988.

The disclosures of all patents, patent applications and any patents which issue therefrom, as well as any corresponding published foreign patent applications, and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

Figure 2:
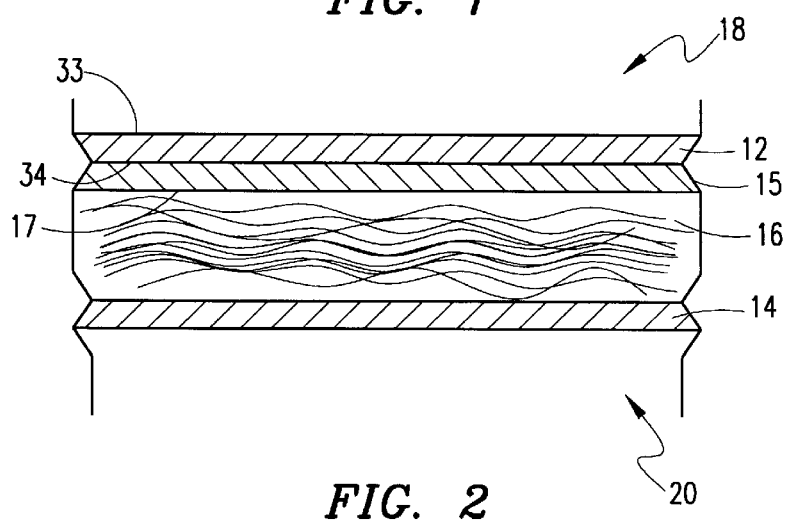
FIG. 2 is a cross sectional schematic view of the absorbent article of FIG. 1 taken along line 2—2 wherein the acquisition distribution layer is of a prior art type.

Referring now to FIG. 1, a simplified representation of a typical absorbent article 10 is shown. It should be understood, however, that FIG. 1 is shown for purposes of example only, and should not be construed to limit the particular type or configuration of absorbent article. As shown in FIG. 2, absorbent article 10 basically comprises topsheet 12, backsheet 14, an acquisition distribution layer 15, and an absorbent core 16. Absorbent core 16 has a top or body facing side 17.

The absorbent article 10 has two surfaces, a body-contacting surface or body surface 18 and a garment-contacting surface or garment surface 20. The body surface 18 is intended to be worn adjacent to the body of the wearer. The garment surface 20 (FIG. 2) of the absorbent article 10 is on the opposite side and is intended to be placed adjacent to the wearer's undergarments or clothing when the absorbent article 10 is worn.

The absorbent article 10 has two centerlines, a longitudinal centerline 22 (FIG. 1) and a transverse centerline 24 (FIG. 1). Absorbent article 10 has two spaced apart longitudinal edges 26 and two spaced apart transverse or end edges, i.e., ends 28, which together form the periphery 30 of the absorbent article 10.

The individual components of the absorbent article 10 will now be looked at in greater detail. Topsheet 12 is compliant, soft-feeling and non-irritating to the wearer's skin. Further, topsheet 12 is liquid permeable, permitting liquids to readily penetrate through its thickness. The topsheet 12 has a body-facing side 33 (FIG. 2) and a garment-facing side 34 (FIG. 2), two longitudinal or side edges 36 and two end edges 38 (FIG. 1). Absorbent core 16 has a top or body facing side 17. Throughout the remainder of this application, similar components will share the same numbers for all embodiments of the invention, e.g., "topsheet" will be designated by the numeral 12 in each embodiment.

Topsheet 12 is preferably made of a nonwoven material or of a vacuum formed film layer. Topsheet 12 may be bonded to acquisition distribution layer 15 (FIG. 2), although in the preferred embodiment, topsheet 12 is not bonded to but instead lays in contact with acquisition distribution layer 15. The absorbent article of FIG. 3 utilizes a three dimensional apertured plastic film 44 as an anti-rewet (or anti-wicking) layer. Three dimensional apertured plastic film 44 has a body facing side or female side 46 and a garment facing side or male side 48. The garment-facing side 34 of the topsheet 12 is preferably maintained in close contact with the female side 46 of the apertured plastic film 44. The topsheet 12 and acquisition distribution layer 15 are examined in greater detail below.

The topsheet 12 may be any nonwoven fabric that is permeable to liquids. A suitable nonwoven fabric may be manufactured from a various materials including natural fibers (e.g., wood or cotton fibers), synthetic fibers (e.g., polyester, polypropylene) or a combination thereof. The topsheet 12 is preferably made from fibers selected from a group consisting of polypropylene, polyester, polyethylene, polyvinylalcohol, starch base resins, polyurethanes, cellulose and cellulose esters.

Various manufacturing techniques may be used to manufacture nonwoven fabric for use in topsheet 12. For example, the nonwoven fabric may be resin-bonded, needle punched, spunbonded, or carded. Carded nonwoven fabrics may be thermally bonded, air-thru bonded, and spunlaced fabrics. A preferred nonwoven fabric is a thermally bonded polypropylene fabric.

A typical topsheet 12 is a non-woven fabric having a pattern of thermal bond sites. One example of a nonwoven fabric has a carded thermally dot bonded polypropylene web. The thermal bonds of such a fabric are typically rectangularly-shaped in plan view. The bonds are typically arranged in staggered rows. Another typical nonwoven is a spunbonded polypropylene web with similarly arranged thermal bonds. Still another typical nonwoven fabric is a carded polypropylene web that is embossed in accordance with the method taught in U.S. Pat. No. 4,781,710 issued to Megison, et al. This nonwoven fabric has embossed and thermal bonded areas that are diamond-shaped in plan view. The diamond-shaped bonds are spaced apart and arranged in a diamond-shaped grid such as is shown in FIGS. 1 and 2 of the Megison, et al. patent. Typically, the embossing does not extend to the underlying core, however.

Preferably, acquisition distribution layer 15 is a perforated thermoplastic film with tapered capillaries which has a run off percent of less than about 10 percent and which has an increased liquid flow rate through the tapered capillaries. The method of making such a film includes a two-fold surface treatment, which is taught by U.S. Pat. Nos. 4,535,020 and 4,456,570 to Thomas et al. entitled, "Perforated Film" and "Treatment of Perforated Film", respectively. U.S. Pat. Nos. 4,535,020 and 4,456,570 are incorporated herein by reference. The method teaches that one surface treatment is provided by adding an internal chemical additive, namely a surfactant, to a film forming polyolefin resin. The additive is compounded or otherwise mixed or blended with the resin prior to the film being formed from the resin. After the film is formed the other surface treatment is accomplished by treating the film with a corona discharge treatment which acts on the chemical additive to provide the perforated film with a zero or near zero percent run off.

The surfactant provides a film surface which has greater polarizability than the polyolefin film would have without the surfactant being added. Higher surface polarity yields higher wettability. Although the chemically treated film is more polar than untreated film, corona discharge treatment of the film itself provides the desired maximum wettability. Any surfactant which achieves this polarity and which migrates to the surface of the film may be used in this invention.

Figure 3:
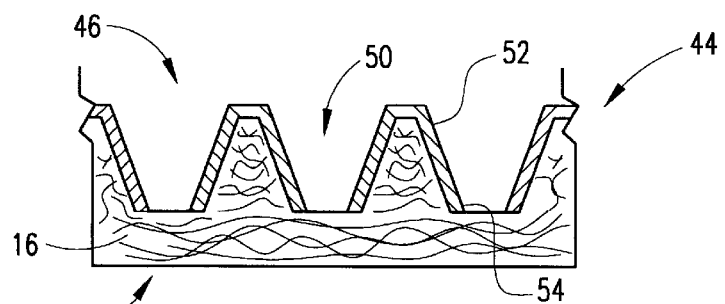
FIG. 3 is an enlarged cross sectional view of the prior art acquisition distribution layer of FIG. 2.

Referring now to FIG. 3, the apertured plastic film 44 is typically located between the topsheet 12 and the absorbent core 16. As shown in FIG. 3, the apertured plastic film 44 is a three-dimensional structure having a plurality of tapered capillaries 50, each of which has a base opening 52, and an apex opening 54. The apex of the openings 54 are in intimate contact with the absorbent core 16. Additionally, most of the surface area of male side 48 of film 44 is in contact with core 16.

The apertured plastic film 44 is typically manufactured from a liquid impervious, thermoplastic material. One suitable material is a low density polyethylene film having a thickness of from 0.001 to 0.002 inches (0.0025 to 0.0051 cm.). The thermoplastic material for use in the manufacture of a typical apertured plastic film 44 is selected from a group consisting generally of polyethylene, polypropylene, polyvinyl chloride, starch base resins, polyvinylalcohol, polyurethanes, polycaprolactone and cellulose esters, or combinations thereof.

In one typical embodiment, the thermoplastic material is provided with a multiplicity of tapered capillaries 50 in a manner, size, configuration, and orientation set forth in U.S. Pat. No. 3,939,135 issued to Thompson on Dec. 30, 1975. Other typical apertured plastic films are disclosed in U.S. Pat. No. 4,324,246, issued to Mullane, et al. on Apr. 13, 1982, U.S. Pat. No. 4,342,314, issued to Radel, et al. on Aug. 3, 1982, and U.S. Pat. No. 4,463,045, issued to Ahr, et al. on Jul. 31, 1984. The apertured plastic film 44 can also consist of other types of apertured plastic films that are not thermoplastic. The type of film used depends on the type of processing that the film and nonwoven components are subjected to during the manufacture of the topsheet 12. Thermoplastic films are typically used when the topsheet 12 and the acquisition distribution layer 15 or film 44 are integrally formed into a composite structure by melting. Other types of apertured films include, but are not limited to hydro-formed films. Hydro-formed films are described in at least some of the following U.S. Pat. Nos.: 4,609,518, 4,629,643, 4,695,422, 4,772,444, 4,778,644, and 4,839,216 issued to Curro, et al., and U.S. Pat. No. 4,637,819 issued to Ouellette, et al.

Typically, the nonwoven fabric of topsheet 12 and the apertured plastic film 44 are placed into a face-to-face relationship. The two components may be secured or unsecured. The two components, if secured, may be secured to each other by various methods. Typical methods for securing the nonwoven fabric and the apertured film 44 include, but are not limited to adhesives, fusion including heat bonding and/or pressure bonding, ultrasonics, and dynamic mechanical bonding.

The adhesives can be applied in a uniform continuous layer, a patterned layer, or an array of separate lines, spirals, beads, or spots of adhesive. The adhesive attachment typically comprises an open pattern network of filaments of adhesive such as is disclosed in U.S. Pat. No. 4,573,986 issued to Minetola, et al. on Mar. 4, 1986, or an open pattern network of filaments having several lines of adhesive filaments swirled into a spiral pattern as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Another method of heat/pressure bonding that could be used is described in U.S. Pat. No. 4,854,984 issued to Ball, et al. on Aug. 8, 1989.

The nonwoven, fabric of topsheet 12 and the apertured plastic film 44 may alternatively be indirectly secured. For example, the nonwoven fabric and the apertured film 44 could be secured to or through a thin layer of airfelt, or a layer-of-hydrophobic material positioned between the nonwoven fabric and the apertured plastic film 44. Typically, such additional layer or layers are treated with a surfactant as described in greater detail below.

The nonwoven fabric of topsheet 12 and the apertured plastic film 44 can alternatively be integrally formed into a composite structure, as taught by Merz et al. in U.S. Pat. No. 4,995,930. The terms "composite", "composite structure" or "combination", as used herein, refer to relationships in which portions of the nonwoven fabric extend into the film 44, and vice versa so that they are integrally attached.

Figure 4:
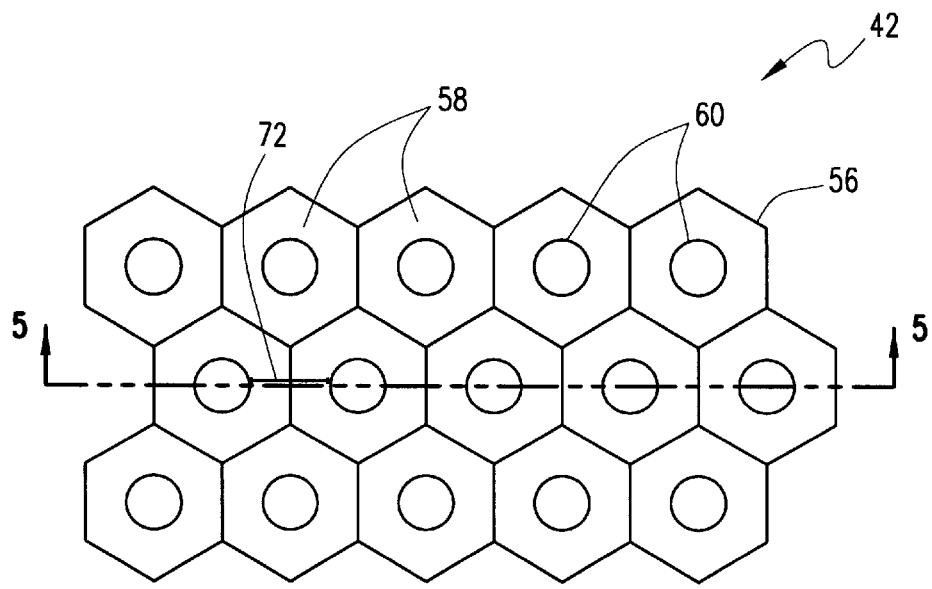
FIG. 4 is a plan view of a three dimensional apertured film of a first embodiment of the invention for use as an acquisition distribution layer in the absorbent article of FIG. 1.
Figure 5:
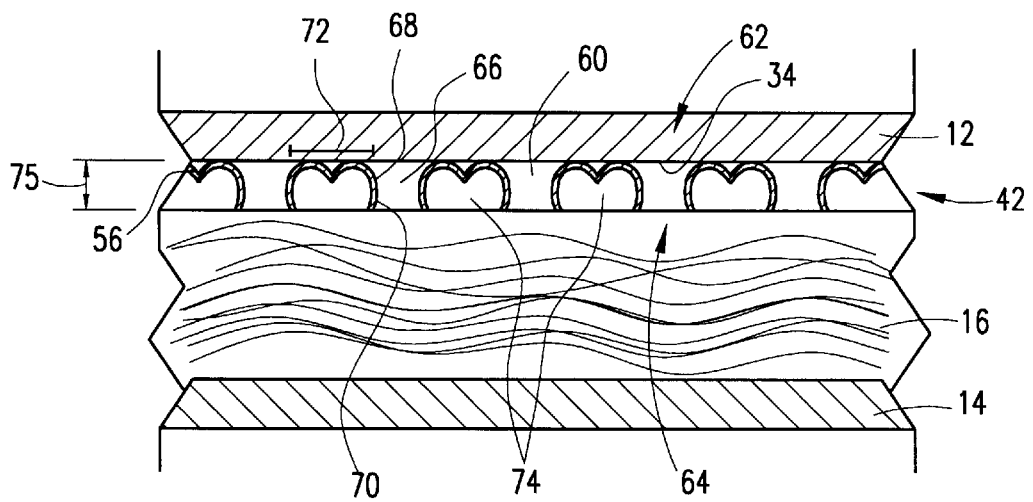
FIG. 5 is a cross sectional view of the absorbent article of FIG. 1 taken along line 2—2 of FIG. 1 wherein the acquisition distribution layer shown is a cross sectional view of the three dimensional apertured film of FIG. 4 taken along line 5—5 of FIG. 4.

Referring now to FIGS. 4 and 5, a first embodiment of an improved absorbent article of the applicant's invention utilizes an acquisition distribution layer 42 made of a three dimensional apertured film 56 imparted with a hexagonal pattern. Although a hexagonal pattern is used for purposes of illustration, it should be understood that other patterns may also be used for any of the films described herein. Examples of other patterns include circular, oval, elliptical, polygonal, or other suitable patterns or combinations of patterns. The hexagonal pattern forms a plurality of adjacent hexagons or cells 58. In the preferred embodiment, the hexagonal pattern is based on a 8.75 mesh wherein "mesh" is the number of cells 58 aligned in a one-inch length. Although a mesh count of 8.75 is preferred, a mesh count of from 2 to 25 or more preferably from 4 to 15 may be used. Preferably, each cell 58 is provided with an aperture 60 that has a large hole diameter, e.g., 59 mils, which are large enough to allow insult fluids to be acquired through the three dimensional apertured film 56 as rapidly as the fluids are delivered.

Referring in particular to FIG. 5, which shows an enlarged cross sectional view of film 56 taken along line 5—5 of FIG. 4, three dimensional apertured film 56 has a body facing side or female side 62 and a garment facing side or male side 64. The garment-facing side 34 of the topsheet 12 is preferably maintained in close contact with the female side 62 of the apertured plastic film 56. Preferably topsheet 12 maintains in contact with film 56 but is unbonded to film 56.

As can be seen in FIG. 5, the film 56 is located between a topsheet 12 and an absorbent core 16. The apertured plastic film 56 is a three-dimensional structure having a plurality of capillaries 66, each of which has a base opening 68 and an apex opening 70. The apex openings 70 of the capillaries 66 are in intimate contact with the absorbent core 16, and preferably apex openings 70 are affixed to core 16 to insure this intimate contact. It should also be noted that essentially only the apex openings 70 of the capillaries 66 are in intimate contact with the core 16, thereby assuring that the void spaces 74 providing for lateral spillage remain substantially unencumbered. A land area 72 is formed between adjacent apertures 60 on the female side 62 of the apertured plastic film 56. A void volume space 74 (FIG. 5) is formed on the male side 64 of the apertured plastic film 56 that provides a fluid passageway between each of the cells 58. Preferably, the ratio of void volume space 74 versus apex opening space 70 is 2:1. The three dimensional apertured film 56 has a loft 75, i.e. the distance between the surface on the female side 62 and the planar surface on the male side 64, of from 0.031" to 0.125", more preferably 0.045" to 0.100", and most preferably of 0.050". The thermoplastic material used in the film 56 preferably has a density in the range of from about 0.919 g/cc to 0.960 g/cc, with the more preferred range of densities being from about 0.930 g/cc to 0.950 g/cc. The general melt indices range for a typical material is preferably from about 0.10 to about 8.50, with the more preferred range typically being from about 1.5 to about 4.5.

Figure 6:
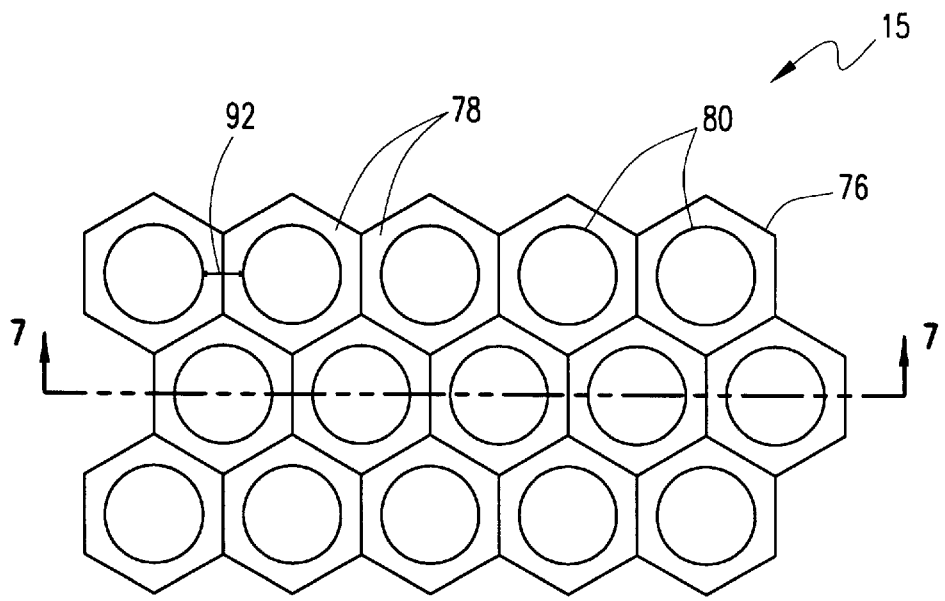
FIG. 6 is a plan view of a three dimensional apertured film of a second embodiment of the invention for use as an acquisition distribution layer in the absorbent article of FIG. 1.
Figure 7:
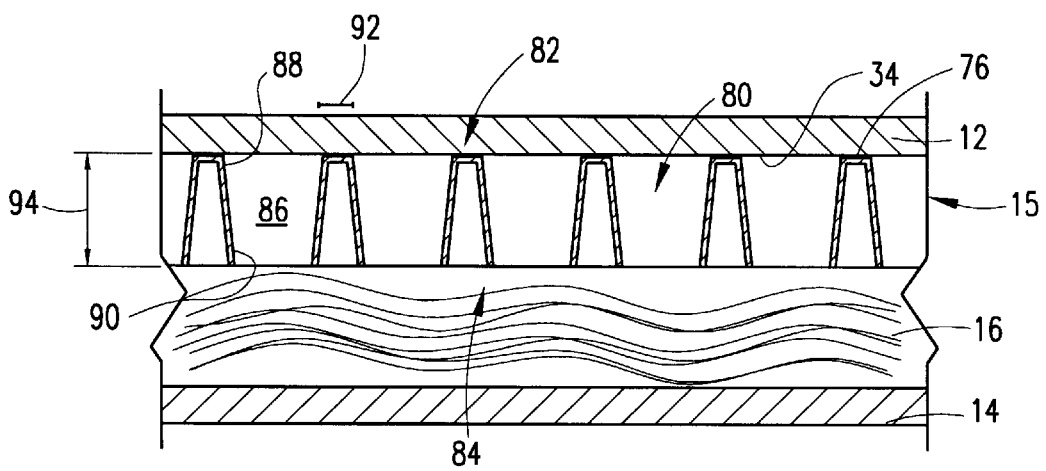
FIG. 7 is a cross sectional view of the absorbent article of FIG. 1 taken along line 2—2 of FIG. 1 wherein the acquisition distribution layer shown is a cross sectional view of the three dimensional layer apertured film of FIG. 6 taken along line 7—7 of FIG. 6.

Referring now to FIGS. 6 and 7, a second embodiment of an improved absorbent article of the applicant's invention utilizes an acquisition distribution layer 15 made of a three dimensional apertured film 76 imparted with a hexagonal pattern. Although a hexagonal pattern is discussed herein, it should be understood that other patterns may also be used. Examples of other patterns include circular, oval, elliptical, polygonal, or other suitable patterns or combinations of patterns. The hexagonal pattern forms a plurality of adjacent hexagons or cells 78. In the preferred embodiment, each cell 78 is $\frac{1}{32}$" to $\frac{1}{2}$" as measured from the flat to flat portion of the hexagon making up each cell 78 of the hexagonal pattern. More preferably, cells 78 of $\frac{1}{16}$" to $\frac{1}{5}$" are used. Still more preferably, cells 78 measuring $\frac{1}{8}$" across are used.

Referring more particularly to FIG. 7, which shows an enlarged cross sectional view of film 76 taken along line 7—7 of FIG. 6, three dimensional apertured film 76 has a body facing side or female side 82 and a garment facing side or male side 84. The garment-facing side 34 of the top layer 12 is preferably maintained in close contact with the female side 82 of the apertured plastic film 76. Preferably, top layer 12 maintains contact with but is unbonded to film 76.

As can be seen in FIG. 7, the film 76 is located between a top layer 12 and an absorbent core 16. The apertured plastic film 76 is a three-dimensional structure having a plurality of large openings or buckets 86, each of which has a base opening 88 and an apex opening 90. The apex openings 90 of buckets 86 are in intimate contact with the absorbent core 16, and preferably apex opening 90 is affixed to core 16 to insure this intimate contact. A land area 92 is formed between adjacent apertures 80 on the female side 82 of the apertured plastic film 76. In the honeycomb embodiment, land area 92 is preferably relatively narrow. The three dimensional apertured film 76 has a loft 94 (FIG. 7), i.e. the distance between the surface on the female side 82 and the planar surface on the male side 84, of greater than 30 mils. In the preferred embodiment, the loft 94 is 50 mils.

Figure 8:
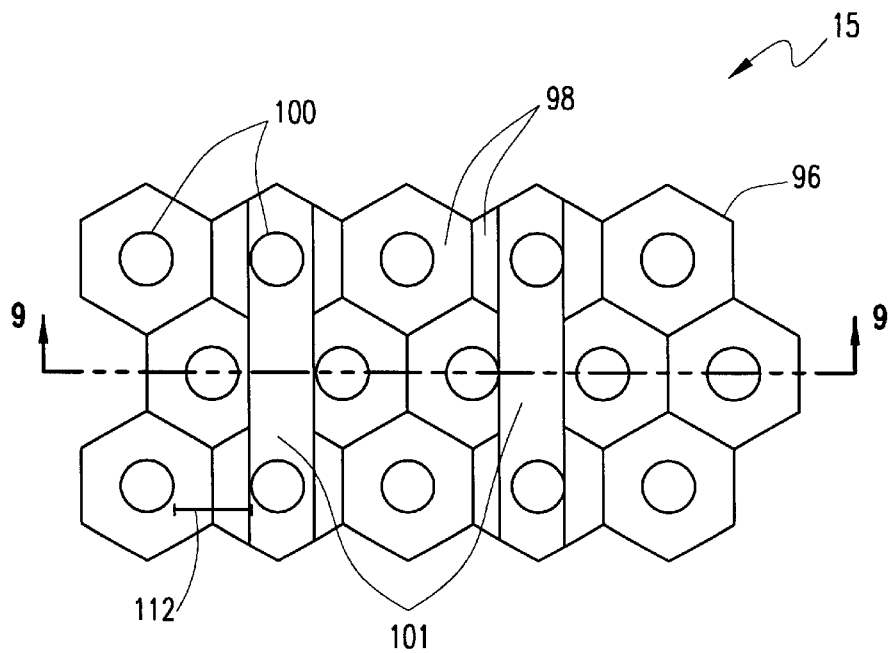
FIG. 8 is a plan view of a three dimensional apertured film of a third embodiment of the invention for use as an acquisition distribution layer in the absorbent article of FIG. 1.
Figure 9:
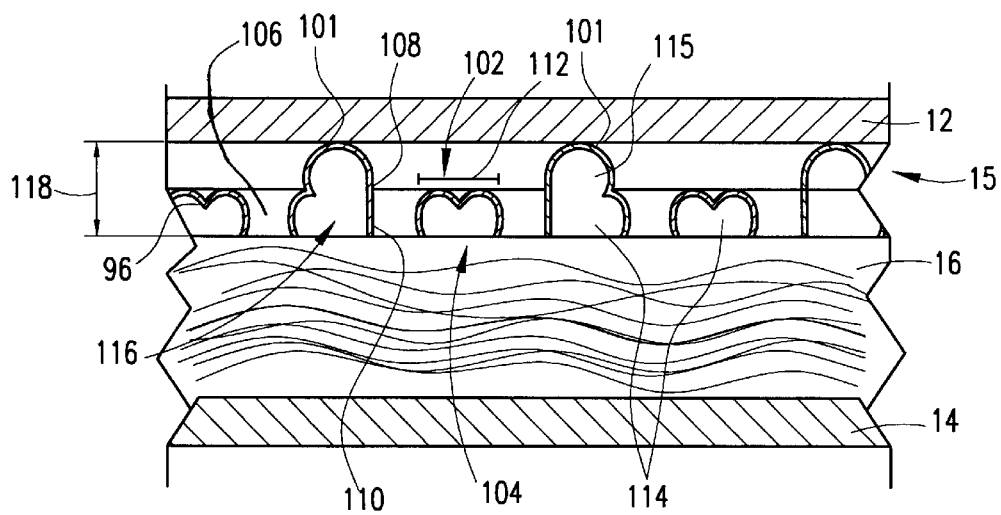
FIG. 9 is a cross sectional view of the absorbent article of FIG. 1 taken along line 2—2 of FIG. 1 wherein the acquisition distribution layer shown is a cross sectional view of the three dimensional layer apertured film of FIG. 8 taken along line 9—9 of FIG. 1.

Referring now to FIGS. 8 and 9, a third embodiment of an improved absorbent article of the applicant's invention utilizes an acquisition distribution layer 15 made of a three dimensional apertured film 96 imparted with a hexagonal pattern. Although a hexagonal pattern is discussed for purposes of illustration, it should be understood that other patterns may also be used for any of the films discussed herein. Examples of other patterns include circular, oval, elliptical, polygonal, or other suitable patterns. The hexagonal pattern forms a plurality of adjacent hexagons or cells 98. In the preferred embodiment, the hexagonal pattern is based on a 8.75 mesh wherein "mesh" is the number of cells 98 aligned in a one-inch length. Although a mesh count of 8.75 is preferred, a mesh count of from 2 to 25 or more preferably from 4 to 15 may be used. Preferably, each cell 98 is provided with apertures 100 that have large hole diameters, e.g., 59 mils. A plurality of raised ridges 101 are formed on the three dimensional apertured film 96. The raised ridges 101 preferably run longitudinally or parallel to longitudinal centerline 22 (FIG. 1) of the absorbent article 10.

Referring in particular to FIG. 9, which shows an enlarged cross sectional view of film 96 taken along line 9—9 of FIG. 8, three dimensional apertured film 96 has a body facing side or female side 102 and a garment facing side or male side 104. The garment-facing side 34 of the topsheet 12 is preferably maintained in close contact with the female side 102 of the apertured plastic film 96. Preferably, top layer 12 maintains contact with but is unbonded to film 96. The thermoplastic material used in the film 76 preferably has a density in the range of from about 0.919 g/cc to 0.960 g/cc, with the more preferred range of densities being from about 0.930 g/cc to 0.950 g/cc. The general melt indices range for a typical material is preferably from about 0.10 to about 8.50, with the more preferred range typically being from about 1.5 to about 4.5.

As can be seen in FIG. 9, the film 96 is located between topsheet 12 and an absorbent core 16. The apertured plastic film 96 is a three-dimensional structure having a plurality of capillaries 106, each of which has a base opening 108 and an apex opening 110. The apex openings 110 of capillaries 106 are in intimate contact with the absorbent core 16, and preferably apex openings 110 are affixed to core 16 to insure this intimate contact. It should also be noted that essentially only the apex openings 110 of capillaries 106 are in intimate contact with the core 16, thereby assuring that the void spaces 114–116 providing for lateral spillage remain substantially unencumbered. A land area 112 is formed between adjacent apertures 100 on the female side 102 of the apertured plastic film 96. A void volume space 114 is formed on the male side 104 of the apertured plastic film 96 that provides a fluid passageway between each of the cells 98. A channel 115 (FIG. 9) is formed on the male side 104 of each raised ridge 101. An enlarged void volume space 116 is formed when the channel 115 communicates with the void volume space 114 of the apertured plastic film 96. The three dimensional apertured film 96 has a loft 118 (FIG. 9), i.e. the distance between the surface on the raised ridges 101 on female side 102 and the planar surface of the male side 104, in the range of 0.065, i.e., the raised ridge 101 preferably adds 0.015" to the preferred loft of 0.050" for film 96. Although 0.050" is the most preferred loft, a loft of from 0.031" to 0.125" and more preferably 0.045" to 0.100" may be used. Raised ridges 101 may be formed by affixing a wire around the circumference of a vacuum forming screen or by forming an elongated protrusion upon a vacuum formed screen and passing a film over the screen in a manner known in the art. The thermoplastic material used in the film 96 preferably has a density in the range of from about 0.919 g/cc to 0.960 g/cc, with the more preferred range of densities being from about 0.930 g/cc to 0.950 g/cc. The general melt indices range for a typical material is preferably from about 0.10 to about 8.50, with the more preferred range typically being from about 1.5 to about 4.5.

Figure 10:
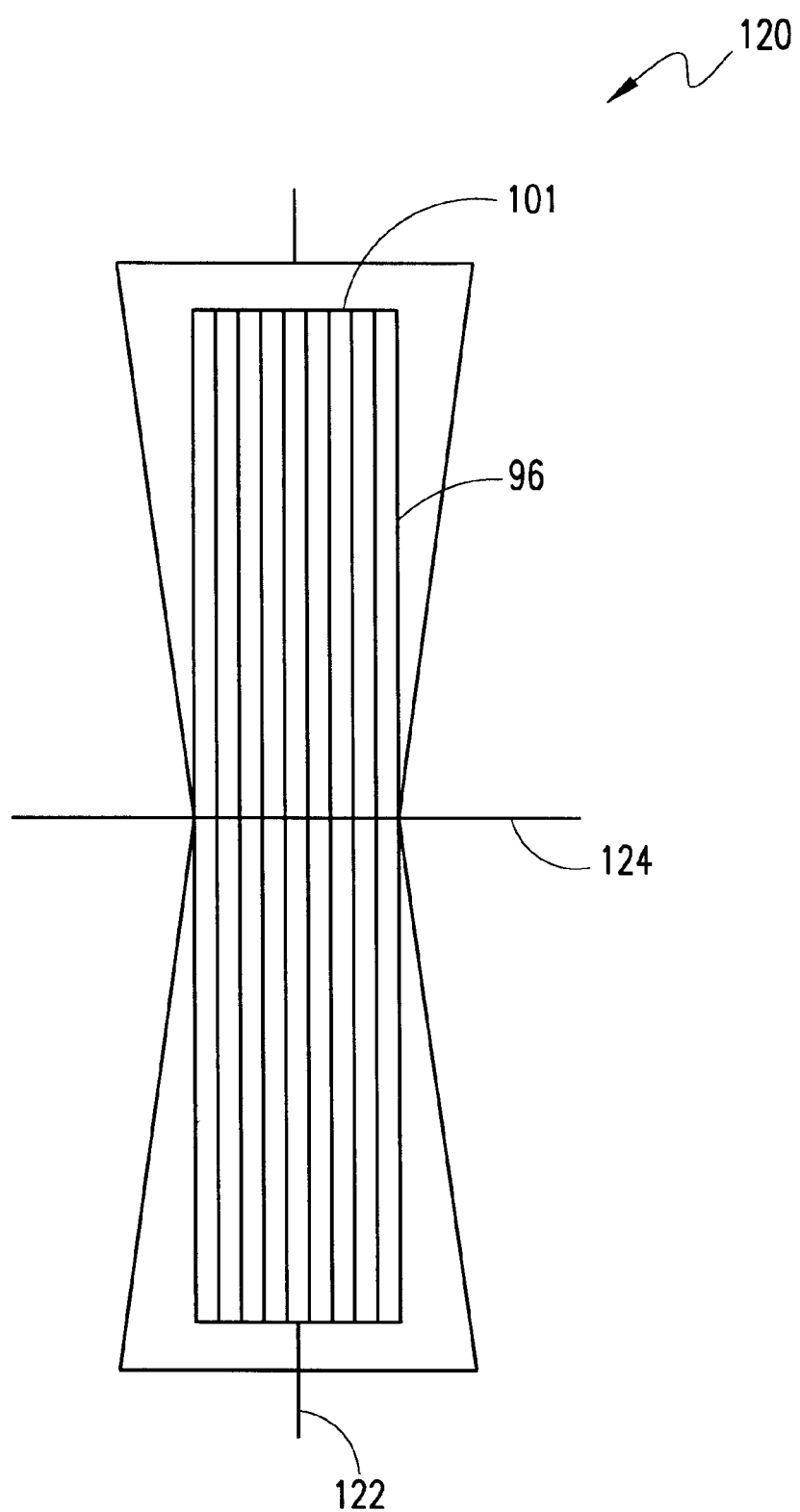
FIG. 10 is a plan view of a disposable diaper utilizing the three dimensional apertured film of FIGS. 8 and 9.

A disposable diaper 120 utilizing a section of three dimensional apertured film 96 having raised ridges 101 is shown in FIG. 10. Disposable diaper 120 has a longitudinal centerline 122 and a transverse centerline 124. It should be understood that disposable diaper 120 is shown here as an example only, and the invention described herein should not be construed to be limited to disposable diapers but may also include incontinent articles, sanitary napkins, pantiliners or other absorbent articles.

Figure 11:
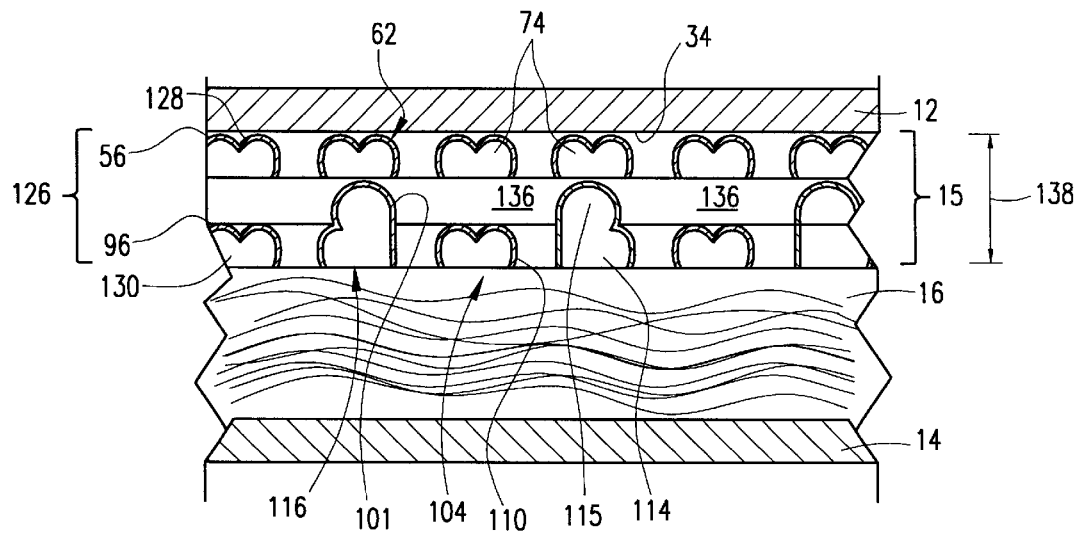
FIG. 11 is a cross sectional view of the absorbent article of FIG. 1 wherein the acquisition distribution layer is a multi-layer apertured film of a fourth embodiment of the invention.

Referring now to FIG. 11, a fourth embodiment of an improved absorbent article of the applicant's invention utilizes an acquisition distribution layer 15 made of three dimensional apertured film 56 (FIGS. 4 and 5) and three dimensional apertured film 96 (FIGS. 8 and 9), which shall be referred to as multi-layer apertured film 126. Three dimensional apertured film 56 forms the body facing sublayer 128 of multi-layer apertured film 126. Three dimensional apertured film 96 forms the garment facing sublayer 130 of multi-layer apertured film 126. The garment-facing side 34 of the topsheet 12 is preferably maintained in close contact with the female side 62 of the apertured plastic film 56 that forms the body facing sublayer 128. Preferably, top layer 12 maintains contact with but is unbonded to sublayer 128.

As can be seen in FIG. 11, the multi-layer apertured film 126 is located between a topsheet 12 and an absorbent core 16. The multi-layer apertured film 126 is a three-dimensional structure that allows fluids to pass therethrough. The three dimensional apertured film 56 that forms the body facing sublayer 128 is in contact with raised ridges 101 that are formed on the sublayer 130. The apex openings 110 of the three dimensional apertured film 96 that forms the garment facing sublayer 130 are preferably in intimate contact with the absorbent core 16. The void volume space 114 and channel 115, which form the enlarged void volume space 116, of the apertured plastic film 96 that forms the garment facing sublayer 130 is complimented by the additional void volume space 74 of three dimensional apertured film 56 that forms the body facing sublayer 128. A further enlarged void volume space 136 is formed by the space between the sublayers 128 and 130 as a result of the height of channels 101. The multi-layer apertured film 126 has a loft 138, i.e. the distance between the female side 62 of the three dimensional apertured film 56 that forms the body facing sublayer 128 and the planar surface of the male side 104, of three dimensional apertured film 96. The preferred loft 138 for the multi-layer apertured film 126 is 0.90", which is the sum of a preferred loft of 50 mils for film 96, 15 mils for raised ridges 101 and 25 mils for top layer 12. Sublayers 128 and 130 of multi-layer film 126 are preferably bonded together in a manner taught by U.S. Pat. No. 5,635,275 to Biagioli, et al., entitled, "Lamination of non-apertured three-dimensional films to apertured three-dimensional films and articles produced therefrom". U.S. Pat. No. 5,635,275 is hereby incorporated by reference. However, the multi-layer film 126 is preferably unbonded to topsheet 12.

Figure 12:
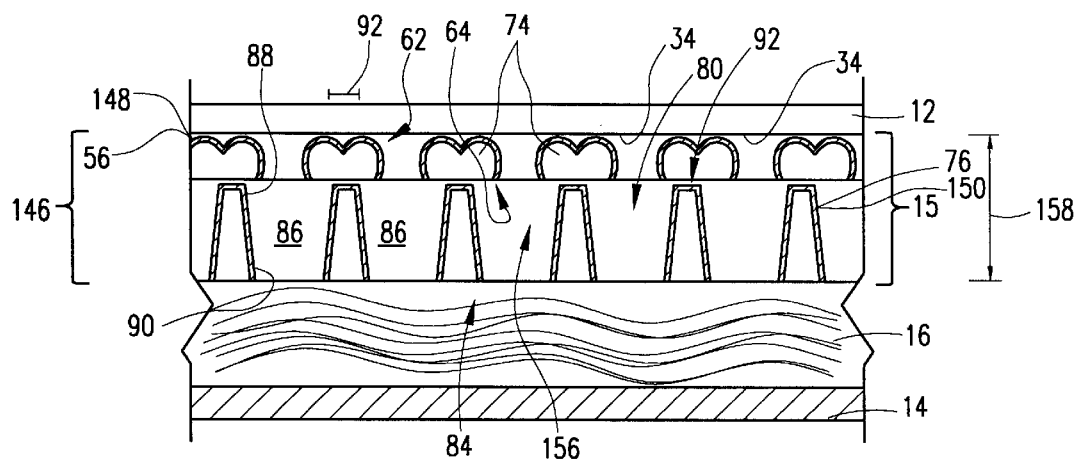
FIG. 12 is a cross sectional view of the absorbent article of FIG. 1 wherein the acquisition distribution layer is a multi-layer apertured film of a fifth embodiment of the invention.

Referring now to FIG. 12, a fifth embodiment of an improved absorbent article of the applicant's invention utilizes an acquisition distribution layer 15 made of three dimensional apertured film 56 (FIGS. 4 and 5) and three dimensional apertured film 76 (FIGS. 6 and 7), which shall be referred to as multi-layer apertured film 146. Three dimensional apertured film 56 forms the body facing sublayer 148 of multi-layer apertured film 146. Three dimensional apertured film 76 forms the garment facing sublayer 150 of multi-layer apertured film 146. The garment-facing side 34 of the topsheet 12 is preferably maintained in close contact with the female side 62 of the apertured plastic film 56 that forms the body facing sublayer 148. Preferably, top layer 12 maintains contact with but is unbonded to sublayer 148.

As can be seen in FIG. 12, the multi-layer apertured film 146 is located between a topsheet 12 and an absorbent core 16. However, it is contemplated that multi-layer apertured film 146 could also function without topsheet 12. The multi-layer apertured film 146 is a three-dimensional structure that allows fluids to pass therethrough. The three dimensional apertured film 56 that forms the body facing sublayer 148 is in contact with land area 92 of three dimensional apertured film 76 that forms the sublayer 150. The body facing sublayer 148 separates the topsheet 12 from unabsorbed fluids that spill over from bucket 86 to an adjacent bucket 86. The void volume space 74 of body facing sublayer 148 and the buckets 86 of garment facing sublayer 150 form a further enlarged void volume space 156. The multi-layer apertured film 146 has a loft 158, i.e. the distance between the female side 62 of the three dimensional apertured film 56 that forms the body facing sublayer 148 and the planar surface of the male side 84, of three dimensional apertured film 76. The preferred loft 158 for the multi-layer apertured film 146 is 70 mils, i.e., 50 mils for the garment facing sublayer 150 and 20 mils for the body facing sublayer 148. Sublayers 148 and 150 of multi-layer film 146 are preferably bonded together in a manner taught by U.S. Pat. No. 5,635,275 to Biagioli, et al., which is hereby incorporated by reference. However, the multi-layer film 146 is preferably unbonded to topsheet 12. The composite multi-layer apertured films 126 and 146 may be constructed in accordance with the teachings of U.S. Pat. No. 5,635,275 to Biagioli, et al., which is hereby incorporated by reference.

Figure 13:
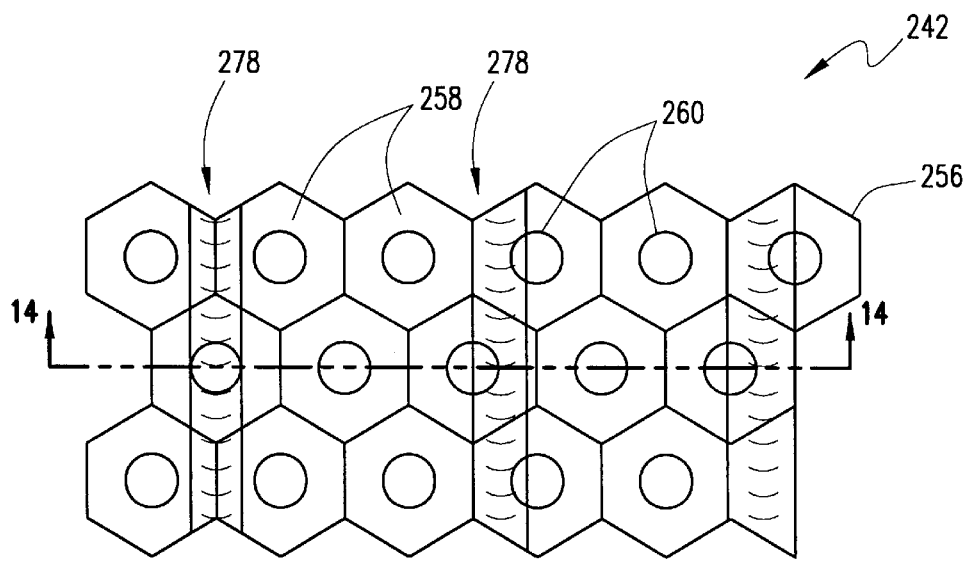
FIG. 13 is a plan view of a three dimensional apertured film of an additional embodiment of the invention having channels formed therein, wherein the three dimensional apertured film is for use as an acquisition distribution layer in the absorbent article of FIG. 1.

Referring now to FIG. 13, a sixth embodiment of an improved absorbent article of the applicants' invention utilizes an acquisition distribution layer 242 made of a three dimensional apertured film 256 imparted with a hexagonal pattern. Although a hexagonal pattern is used for purposes of illustration, it should be understood that other patterns may also be used for any of the films described herein. Examples of other patterns include circular, oval, elliptical, polygonal or other suitable patterns or combinations of patterns. The hexagonal pattern forms a plurality of adjacent hexagons or cells 258. In the preferred embodiment, the hexagonal pattern is based on a 8.75 mesh wherein "mesh" is the number of cells 258 aligned in a one inch length. Although a mesh count of 8.75 is preferred, a mesh count from 2 to 25 and more preferably from 4 to 15 may be used. Preferably, each cell 258 is provided with an aperture 260 that has a large hole diameter, e.g., 59 mils, which is large enough to allow insult fluids to be acquired through the three dimensional apertured film 256 as rapidly as the fluids are delivered. This embodiment provides channels 278. Channels 278 provide a path way for fluid flow and direct fluid flow in preferred directions.

Figure 14:
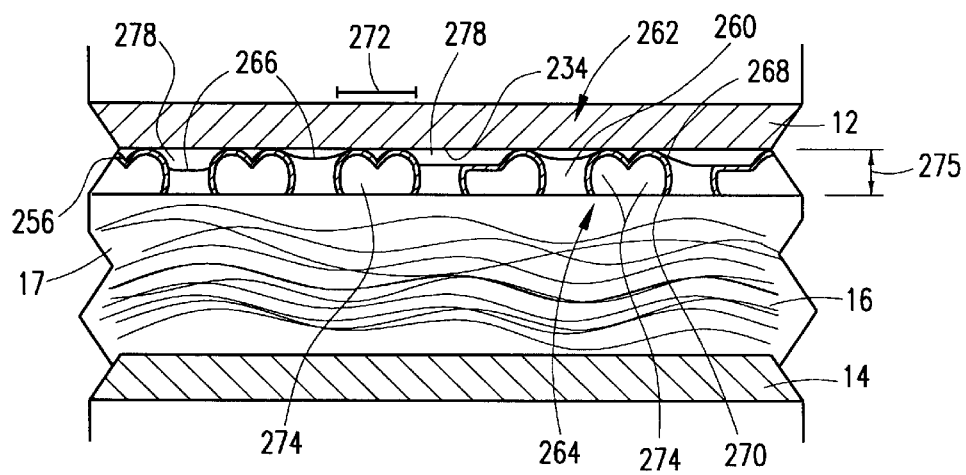
FIG. 14 is a cross-sectional view of the absorbent article of FIG. 1 taken along line 2—2 of FIG. 1 when the acquisition distribution layer shown is a cross-sectional view of the channeled three dimensional apertured film of FIG. 13 taken along line 14—14 of FIG. 13.

Referring now particularly to FIG. 14, which shows an enlarged cross sectional view of film 256 taken along line 14—14 of FIG. 13, a three dimensional apertured film 256 has a body facing (female) side 262 and a garment facing (male) side 264. The garment facing side 234 of the top sheet 12 is preferably maintained in close contact with the female side 262 of the apertured plastic film 256. Preferably top sheet 12 maintains contact with film 256, but is unbonded to film 256.

As can be seen in FIG. 14, the film 256 is located between a top sheet 12 and an absorbent core 16. The apertured plastic film 256 is a three dimensional structure having a plurality of capillaries 266, each of which has a base opening 268 and an apex opening 270. The apex openings 270 of the capillaries 266 are in intimate contact with the absorbent core 16 and preferably apex openings 270 are affixed to core 16 to ensure this intimate contact. It should also be noted that essentially only the apex opening 270 of the capillaries 266 are in intimate contact with the core 16, thereby assuring that the void space 274, which provides for lateral spillage, remains substantially unencumbered. A land area 272 is formed between adjacent apertures 260 on the female side 262 of the apertured plastic film 256. A void volume space 274 (FIG. 14) is formed on the male side 264 of the apertured plastic film 256 that provides a fluid passageway between each of the cells 258. Preferably, the ratio of void volume space 274 versus apex opening space 270 is 2:1. The three dimensional apertured film 256 has a loft 275, i.e., the distance between the surface on the female side 262 and the planar surface on the male side 264, from 0.031" to 0.125", more preferably 0.045" to 0.100", and most preferably of 0.050". The channels 278 are preferably about ⅓ of the total loft 275 of the acquisition distribution layer (ADL). Channel depths of ⅛ of the total loft 275 will show some effect, as well. In a preferred embodiment, a 50 mil ADL loft, 8.75 hex material has a nominal channel depth of 15 mils. The channels 278 are preferably spaced about ¼ inch apart on centers and are approximately 1/16 inches wide. Spacing as tight as ⅛ inch apart can be utilized, and channel widths from 1/32 inch to ¼ inch can be applied.

The thermoplastic material used in the film 256 preferably has a density in the range from 0.919 g/cc to 0.960 g/cc, with a more preferred range of densities being from about 0.930 g/cc to 0.950 g/cc. The general melt indices range for a typical material is preferably from about 0.10 to about 8.50, with the more preferred range typically being from about 1.5 to about 4.5.

The preferred method of preparing channeled films is to position a forming cylinder on a lathe. The cylinder is then rotated and channels are ground into the screen's outer diameter to desired depths. It is also preferred, but not essential, to provide the cylinder with an internal mandrel for maintaining True Indicated Runout (TIR). This will minimize the difficulty of grinding the channels to a consistent depth around the circumference of the cylinder. The practical depth limit of a channel is ½ the loft. This limitation is realized because of the forming screen's limitation of being machined in order to provide the forming pattern for channels. If you cut more than half the depth of the forming cylinder, you will weaken it beyond its economical use potential.

Figure 15:
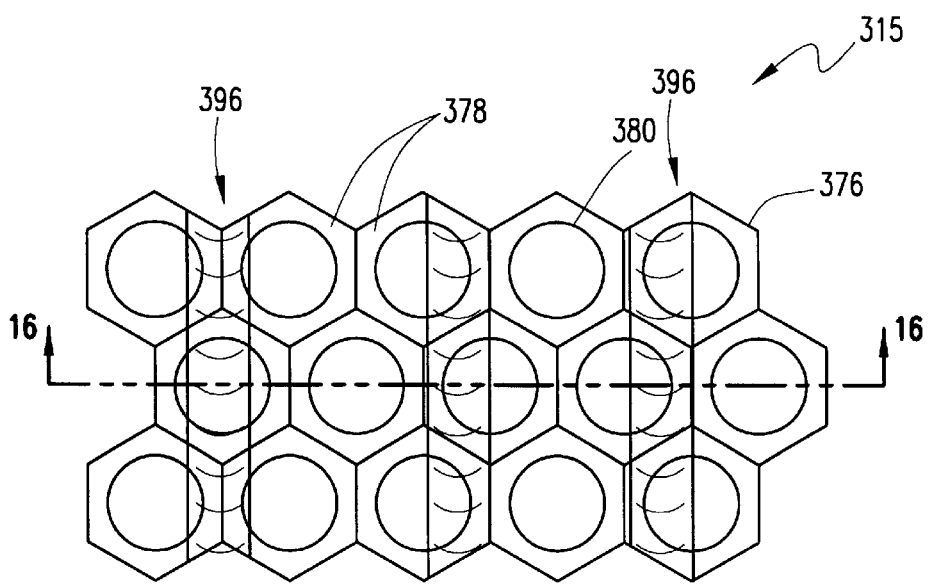
FIG. 15 is a plan view of a three dimensional apertured film of an additional embodiment of the invention having channels formed therein, wherein the three dimensional apertured film is for use as an acquisition distribution layer in the absorbent article of FIG. 1.
Figure 16:
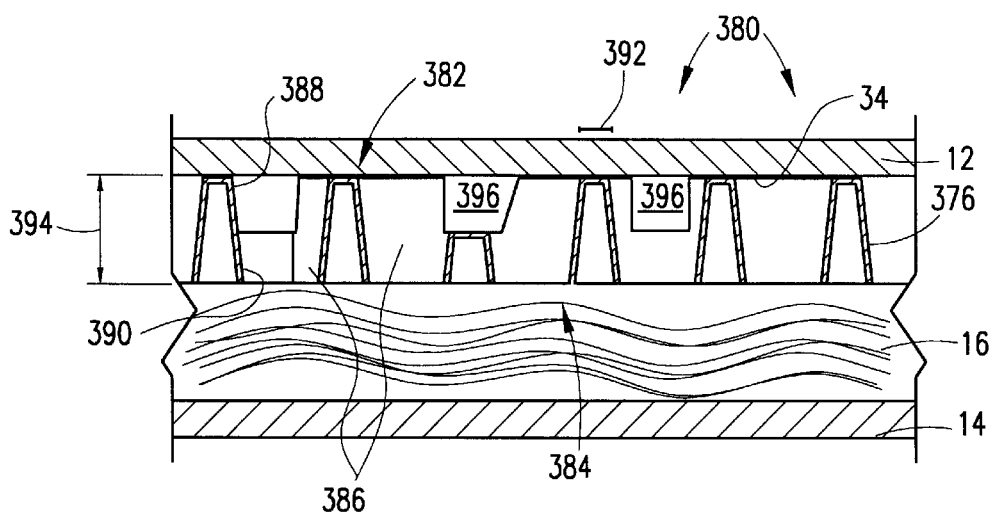
FIG. 16 is a cross-sectional view of the absorbent article of FIG. 1 taken along line 2—2 of FIG. 1 wherein the acquisition distribution layer shown is a cross-sectional view of the channeled three dimensional layer apertured film of FIG. 15 taken along line 16—16 of FIG. 15.

Referring now to FIGS. 15 and 16, a seventh embodiment of an improved absorbent article of the Applicants' invention utilizes an acquisition distribution layer 315 made of a three dimensional apertured film 376 imparted with a hexagonal pattern. Although a hexagonal pattern is discussed herein, it should be understood that other patterns may be used. Examples of other patterns include circular, oval, elliptical, polygonal, or other suitable patterns or combinations of patterns. The hexagonal pattern forms a plurality of adjacent hexagons with cells 378. In a preferred embodiment, each cell 378 is ⅟₃₂ inch to ½ inch as measured from the flat to flat portion of the hexagon making of each cell 378 of the hexagonal pattern. More preferably, cells 378 of ⅟₁₆ inch to ⅕ inch are used. Still more preferably cells 378 measuring ⅛ inch across are used.

Referring more particularly to FIG. 16, which shows an enlarged cross sectional view of the film 376 taken along line 16—16 of FIG. 15, three dimensional apertured film 376 has a body facing (female) side 382 and garment facing (male) side 384. The garment side 34 of the top layer 12 is preferably maintained in close contact with the female side 382 of the apertured plastic film 376. Preferably, top layer 12 maintains contact with, but is unbonded, to film 376.

As can be seen in FIG. 16, the film 376 is located between a top layer 12 and an absorbent core 16. The apertured plastic film 376 is a three dimensional structure having a plurality of large openings or buckets 386, each of which has a base opening 388 and an apex opening 390. The apex opening 390 of a bucket 386 is in intimate contact with the absorbent core 16, and preferably apex opening 390 is affixed to core 16 to ensure this intimate contact. A land area 392 is formed between adjacent apertures 380 on the female side 382 of the apertured plastic film 376. In the honeycomb embodiment, land area 392 is preferably relatively narrow. The three dimensional apertured film 376 has a loft 394 (FIG. 16), i.e., the distance between the surface on the female side 382 and the planer surface on the male side 384, of greater than 30 mil). In the preferred embodiment, the loft 394 is 50 mils. Channels 396 are cut below the plane of the female side 382. Channels 396 provide a spill over space for fluid flow and directs the fluid in preferred directions. The preferred depth of channels 396 is ⅓ the total loft of the ADL. Channel depths of ⅛ of the total loft 394 will show some effect, as well.

In practice, the three dimensional apertured films 56, 76, 96 and multi-layer apertured films 126 and 146 may be used as an acquisition distribution layer 15 in an absorbent article 10. Absorbent article 10 is used for applications where fluid absorption is desirable. In use, body exudates, such as an urine insults from male or female babies or adults, are deposited on the absorbent article 10. The urine insults are typically delivered in a generally singular point of fluid flow. Upon repeated insults, an undesirable leakage or undesirable feeling of wetness by the user may occur due to the core material 16 becoming saturated in the repeat insult region. In other words, the absorbent core 16 may experience an inability to absorb repeated insults in a particular region. As a result, additional fluid insults that are delivered to the absorbent article 10 may be unabsorbed by the core 16 and remain on the top or body facing side 17 of the core layer 16. Applicant's invention provides a method for the unabsorbed fluid from the core layer 16 to be directed to unsaturated zones of the core layer 16. Narrow land areas 92 on the female side 82 of film 76 preferably have a small enough surface area such that fluid contained thereon is insufficient in amount to provide a wetness sensation to the user when portions of the topsheet 12 are momentarily wetted by the spill over of unabsorbed fluid from one bucket 86 to an adjacent bucket 86. When unabsorbed fluid contacts topsheet 12 an unpleasant feeling of wetness of topsheet 12 occurs. A wet topsheet 12 results in uncomfortable fluid contact with the skin of a wearer.

For example, when three dimensional apertured film 56 (FIGS. 4 and 5) is used in absorbent article 10 (FIG. 1), fluid that is not absorbed or that spills-over from core layer 16 is able to flow within void volume space 74 to an unsaturated area of core 16. The void volume space 74 on the male side 64 (FIG. 5) of adjacent cells 58 (FIG. 4) are interconnected to allow a high volume of fluid to pass to unsaturated regions of core 16. The plurality of adjacent hexagons form a large under-side void volume space that provides space for fluid that spills over the top plane or body facing side 17 of saturated core regions 16 and find new, unsaturated regions. The unabsorbed fluid that results from repeated insults may then flow from a saturated zone of absorbent core material 16 and be redirected through the under-side void volume space 74 to an unsaturated zone of the absorbent core material 16. Without the void volume space 74 of the three dimensional apertured film 56, the topsheet 12, which is contact with the skin, will become wet as the insult fluid seeks new regions to be absorbed. The male side void volume area 74 is a much greater total void volume area than previously known anti-rewet or anti-wicking layers.

As another example, when three dimensional apertured film 76 (FIGS. 6 and 7) is used in absorbent article 10 (FIG. 1), insult fluid that is delivered to an area after core material 16 in the area has been saturated pools within buckets 86. When a bucket 86 at the insult point becomes full, buckets 86 adjacent to the insult point are filled as the fluid within full bucket 86 spills over. This process is repeated as spill-over occurs between adjacent buckets 86 to accommodate the full insult fluid volume. Eventually, the spill-over from buckets 86 flows into a bucket 86 that is located proximate an area of unsaturated core material 16 and the fluid is absorbed. Since the spill over of unabsorbed fluid from a bucket 86 to adjacent buckets 86 disperses the unabsorbed liquid over a larger area of core material 16 where the fluid may be absorbed, an undesirable wetness of the topsheet 12 may be avoided. The open-cell void volume areas 86, is much more total void volume area than previously known film anti-rewet or anti-wicking layers. The preferred percentages range of land areas 92 for three dimensional apertured film 76 is 5 to 20% of the total surface area. The large patterned acquisition distribution layer material or three dimensional apertured film 76 also provides a greater measure of loft, e.g. greater than 30 mils and more preferably, 50 mils in the ⅛" honeycomb embodiment. The greater loft 94 or thickness between the upper-most plane and lower-most plane of the of the three dimensional apertured film 64 provides a 'wick-proof' barrier or layer between the wetted core 16 and the skin contact area of a user. A greater loft 94 results in an improved feeling of dryness. Since the material in the topsheet 12 is only a small percent of the total occupied volume, the greater the volume, the more "air cushion" that is provided next to the skin contact region.

As a still further example, when three dimensional apertured film 96 (FIGS. 8 and 9) is used in absorbent article 10 (FIG. 1), insult fluid that is not absorbed in core layer 16 is able to flow within void volume space 114. The void volume space 114 on the male side 104 (FIG. 9) of adjacent cells 98 (FIG. 9) are interconnected to allow a high volume of fluid to pass to unsaturated regions of core 16. Additionally, raised ridges 101 form channels 115 to further accommodate unabsorbed fluids via enlarged void volume space 116. A further advantage of the channels 115 is that the channels 115 direct unabsorbed fluids in a desired direction, such as in the longitudinal direction, i.e., parallel to longitudinal centerline 122 of disposable diaper 120 (FIG. 10). By directing the unabsorbed fluid in the longitudinal direction, the fluid may be directed to locations with greater amounts of unsaturated core material 16 as opposed to directing the fluid towards undesirable locations such as a perimeter of the diaper. The channels 115 direct fluid away from a direction that is parallel to the transverse centerline of disposable diaper 120. The raised ridges are, therefore, effective at eliminating side leakage from disposable diaper 20.

Additionally, various embodiments of acquisition distribution layer 42 may be combined into a multi-layer apertured film, such as film 126 (FIG. 11) or film 146 (FIG. 12). Multi-layer apertured film 126 provides a further enlarged void volume space 136 to accommodate unabsorbed fluids. The further enlarged void volume space 136 allows unabsorbed fluids to flow to regions where core material 16 is unsaturated without allowing the unabsorbed fluids to come into contact with the topsheet 12, thereby avoiding an unpleasant feeling of wetness for the user.

Multi-layer apertured film 146 (FIG. 12) provides a further enlarged void volume space 156 to accommodate unabsorbed fluids. The further enlarged void volume space 156 allows unabsorbed fluids to spill over lands 92 from buckets 86 to adjacent buckets 86 where core material 16 is unsaturated. Body facing sublayer 148, i.e. film 56, substantially prevents unabsorbed fluids from contacting the topsheet 12 when unabsorbed fluids spill over land 92 from a bucket 86 of garment facing sublayer 150, i.e. film 76, to adjacent buckets, thereby further reducing the unpleasant feeling of wetness for the user.

As a further example, when three dimensional channeled apertured film 256 (FIGS. 13 and 14) is used in absorbent article 10 (FIG. 1), insult fluid that is not absorbed when it spills over from core layer 16 is able to flow within void volume space 274 to an unsaturated area of core 16. The void volume space 274 on the male side 264 (FIG. 14) of adjacent cells 158 (FIG. 13) are interconnected to allow a high volume of fluid to pass to unsaturated regions of core 16. The plurality of adjacent hexagons form a large under side void volume space that provides space for fluid that spills over the top plane or body facing side 17 of saturated core region 16 to find new unsaturated regions. Additionally, the channels 278, which are cut below the top plane of the apertured film 256 provide a void space for facilitating increased fluid flow and to direct the fluid in preferred directions. The unabsorbed fluid that results from repeated insults may then flow from a saturated zone of absorbent core material 16 and be redirected through the under side void volume space 274 to an unsaturated zone of the absorbent core material 16. Additionally, without the void volume space 274 of the three dimensional apertured film 256, the top sheet 12 which is in contact with the skin, will become wet as the insult fluid seeks new regions to be absorbed. The male side void volume area 274 has a much greater total void volume area than previously known in anti-rewet or anti-wicking layers. Further, the addition of channels 278 add a significant spill over value. In the preferred embodiment, a 50 mil ADL loft, 8.75 hex material has a nominal channel depth of 15 mils. Channels are spaced about ¼ inch apart on the centers and are approximately ¹⁄₁₆ inch wide. Spacing as tight as ⅛ inch apart can be utilized, and channel widths from ¹⁄₃₂ inch to ¼ inch can be applied.

As a still further example, when three dimensional apertured film 176 (FIGS. 15 and 16) is used in absorbent article 10 (FIG. 1), insult fluid that is delivered to an area after core material 16 in the area has been saturated pools within buckets 386. When a bucket 386 at the insult point becomes full, buckets 386 adjacent to the insult point are filled as the fluid within full buckets 386 spills over. This process is repeated as spill over occurs between adjacent buckets 386 to accommodate the full insult fluid volume. Eventually the spill over from adjacent buckets 386 flows into a bucket 386 that is located approximate an area of unsaturated core material 16 and the fluid is absorbed. Since the spill over of unabsorbed fluid from a bucket 386 to adjacent buckets 386 disperses the unabsorbed liquid over a larger area of core material 16 where the fluid may be absorbed, an undesirable wetness of the top sheet 12 maybe avoided. The open cell void volume areas 386 is much more total void volume area than previously known film anti-rewet or anti-wicking layers. Further, the addition of channels 396 provides a preferred directional pathway for spill over into the next bucket 386, as well as an increased volumetric pathways to spill and redistribute the fluid. Preferably, channels 396 are spaced ¼ inch apart on centers and are approximately ¹⁄₁₆ inch wide. Spacing as tight as ⅛ inch apart can be utilized and channel widths from ¹⁄₃₂ inch to ¼ inch can be applied. The preferred percentages range for land areas 382 for three dimensional apertured film 376 is 5 to 20% of the total surface area. The large patterned acquisition distribution layer material of three dimensional apertured film 376 also provides a greater measure of loft, e.g., greater than 30 mils and more preferably, 50 mils in the ⅛ inch honeycomb embodiment. The greater loft 394 or thickness between the uppermost plane and lowermost plane of the three dimensional apertured film 364 provides a "wick proof" barrier or layer between the wetting core 16 and the skin contact area of a user. A greater loft 394 results in an improved feeling of dryness. Since the material on the top sheet 12 is only a small percentage of the total occupied volume, the greater the volume, the more "air cushion" that is provided next to the skin contact region.

The use of three dimensional apertured films 56, 76, 96, and multi-layer apertured films 126 and 146 increase the loft of the acquisition distribution layer 15 of the absorbent article 10. The greater loft 75, 94, 118, 138 and 158 or thickness between the upper-most plane and lower-most plane of the of the three dimensional apertured films 56, 76, 96, and multi-layer apertured films 126 and 146 provides a 'wick-proof' barrier or layer between the wetted core 16 and the skin contact area of a user. A greater loft 75, 94, 118, 138 and 158 results in an improved feeling of dryness. Since the material in the topsheet 12 is only a small percent of the total occupied volume, the greater the volume, the more "air cushion" that is provided next to the skin contact region.

The large female side void volume of the "spill-over" embodiments facilitates dispersion of unabsorbed fluids. Preferably, for a square meter of film, the female side void volume is greater than 500 cm³, more preferably greater than 750 cm³, and most preferably greater than 1000 cm³. Additionally, the large male side void volume of the "spill-under" embodiments also facilitates dispersion of unabsorbed fluids. Preferably, for a square meter of film, the male side void volume is preferably greater than 500 cm³, more preferably greater than 600 cm³, and most preferably greater than 750 cm³.

Test Data

Testing was performed using the Multiple Insult Acquisition method. Several methods are described in detail in an article by James P. Hanson in an article appearing in Nonwovens World, Fall 1997, page 57–63, entitled, "The Test Mess Part III—Credible Testing for Liquid Acquisition", which is incorporated herein by reference.

Figure 17:
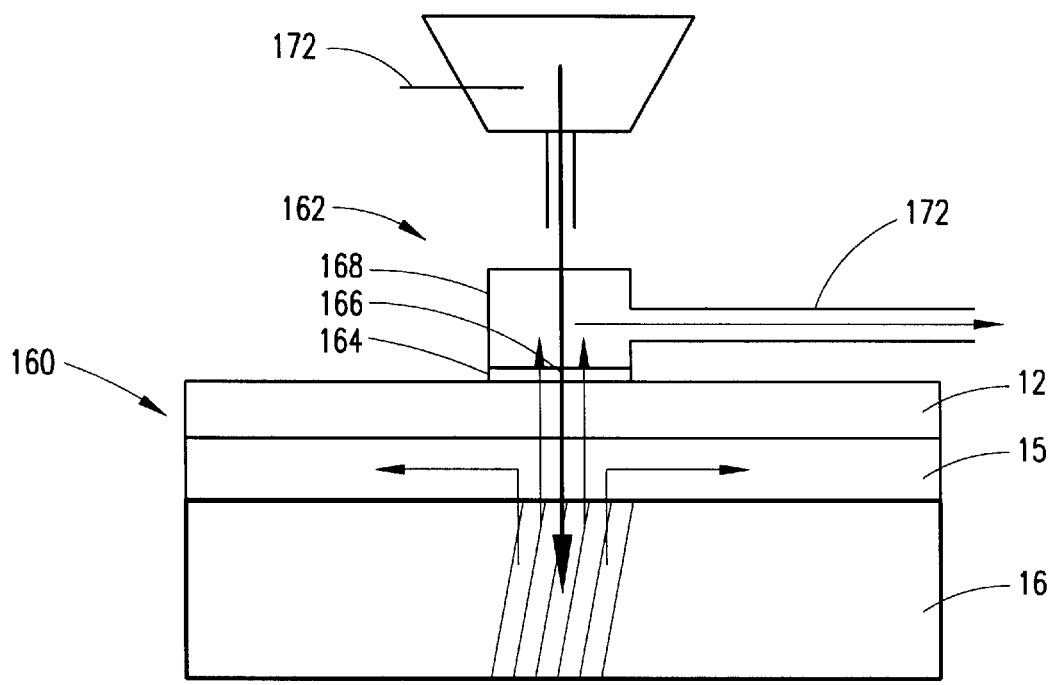
FIG. 17 is a schematic drawing an Liquid Acquisition Apparatus that is used to test the various embodiments of the absorbent articles of FIGS. 1–12.

More specifically, the applicant's test was conducted as follows. Referring now to FIG. 17, die cut samples 160 are cut from absorbent article 10 in an area where acquisition distribution layer 15 is present. The topsheet 12 and acquisition distribution layer 15 are removed from the absorbent article 10, paying particular attention not to change the orientation of the materials. The topsheet 12 and acquisition distribution layer 15 of the core cuts or die samples 160 are then randomly weighed and the average weight and standard deviation for the weight are randomly recorded. Each die cut sample 160 is then reconstructed by adding the absorbent core 16.

To perform the Acquisition Rate Performance on all three layers, a Liquid Acquisition Apparatus 162 is used. Apparatus 162 is made up of a plate 164 having an opening 166 in the center of the plate 164 for placement on top of sample 160. A controlled volume chamber 168 extends upwardly from the plate 164 for receiving a desired fluid flow rate and dosage from a fluid supply 170. An overflow pipe 172 extends outwardly from the controlled volume chamber 168 at a location slightly above the plate 164.

Six samples were tested by the above described method wherein the fluid supply 170 pumped fluid into the controlled volume chamber 168 at a rate of 7 ml/sec. Samples 1–3 are samples having an acquisition distribution layer similar to that shown in FIG. 3 wherein the samples have varying amounts of loft or thickness as is indicated in Table 1, below. In particular, Sample 1 is a prior art film in accordance with the teachings of United States Invention Registration no. H1670, to Aziz et al. having 20 mils of loft, a pattern of round or hex cells and a 22 mesh count. Sample 2 is a prior art film in accordance with the teachings of United States Invention Registration no. H1670, to Aziz et al. having 23 mils of loft, a pattern of hex cells and a 25 mesh count. Samples 4 and 5 are examples of films embodying the invention of the application wherein Sample 3 has an acquisition distribution layer 15 with male side void volume flow area similar to that shown in FIGS. 4 and 5. Sample 4 is the embodiment of the invention shown in FIGS. 6 and 7, i.e., the "bucket" embodiment, having a ⅛" honeycomb pattern on the acquisition distribution layer. Sample 3 has slightly lower loft (it is 49 mils vs. 51 mils) but a greater male side void volume than Sample 4. In particular, Sample 3 has a hex pattern with 50 mils loft on a 8.75 mesh count. Sample 4 has a ⅛" honeycomb pattern with 50 mils of loft on an 8 mesh count. The results are shown in Table 1, below.

| Sample No. | Total Fluid Overflow (ml) | Inverse Expanded Loft (1/mm) | Loft (mm) | Mesh |
|---|---|---|---|---|
| Sample 1 | 62.71 | 0.787402 | 20 | 22 |
| Sample 2 | 59.09 | 0.905512 | 23 | 25 |
| Sample 3 | 54.15 | 1.929134 | 49 | 8.75 |
| Sample 4 | 52.65 | 2.007874 | 51 | 8 |

Figure 18:
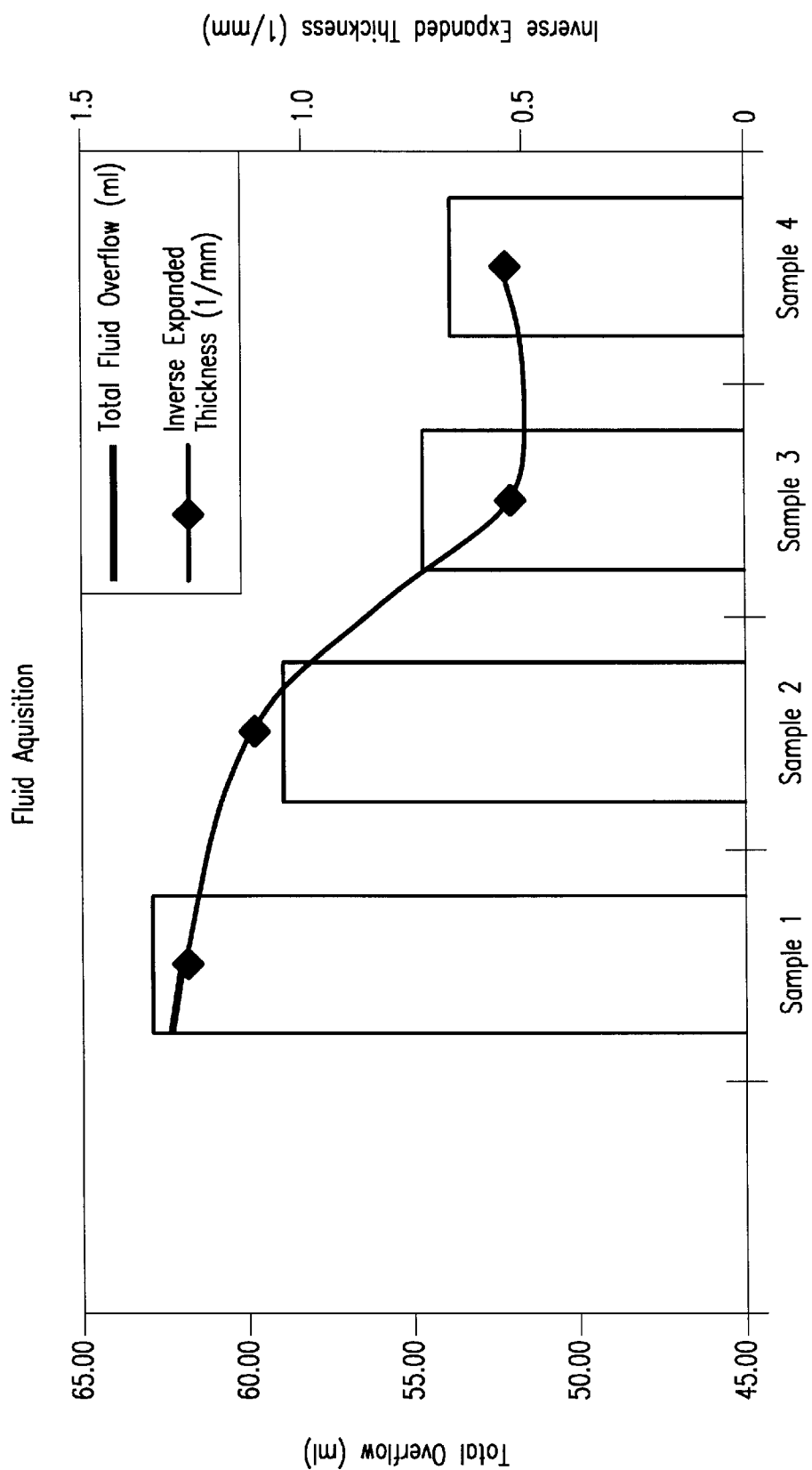
FIG. 18 is a graphical representation of data from Table 1 that shows Total Fluid Overflow and Inverse Loft for various samples of absorbent articles shown in FIGS. 1–12.

The results of the test is shown graphically in FIG. 18. FIG. 18 is comprised of a bar graph that shows fluid overflow (ml) for each sample 1–4. Additionally, FIG. 18 is comprised of a line graph that shows the inverse of the expanded thickness or loft of each sample. Overflow is defined as fluid that flows out of overflow pipe 172 of the Liquid Acquisition Apparatus 162 when 15 mL amount of fluid is delivered at 7 ml/sec into controlled volume chamber 168. The fluid that does not flow through overflow pipe 172 is absorbed by the sample 160.

It can be seen from FIG. 18, that the greater the loft for a particular sample, the less fluid overflow that is observed for a particular sample. The films of applicant's invention, i.e. Samples 3 and 4 have a markedly greater loft than the films having the prior art design, i.e. Samples 1 and 2. Samples 3 and 4 show a markedly lower amount of fluid overflow. It should be noted that the total void volume for Samples 1 and 2 is less than 550 cc/m² of sample material while the total void volume for Samples 3 and 4, which illustrate embodiments of applicant's invention, is more than 1000 cc/m². The preferred total void volume for applicant's invention is greater than 750 cc/m², more preferably greater than 875 cc/m², and most preferably greater than 1000 cc/m².

Figure 19:
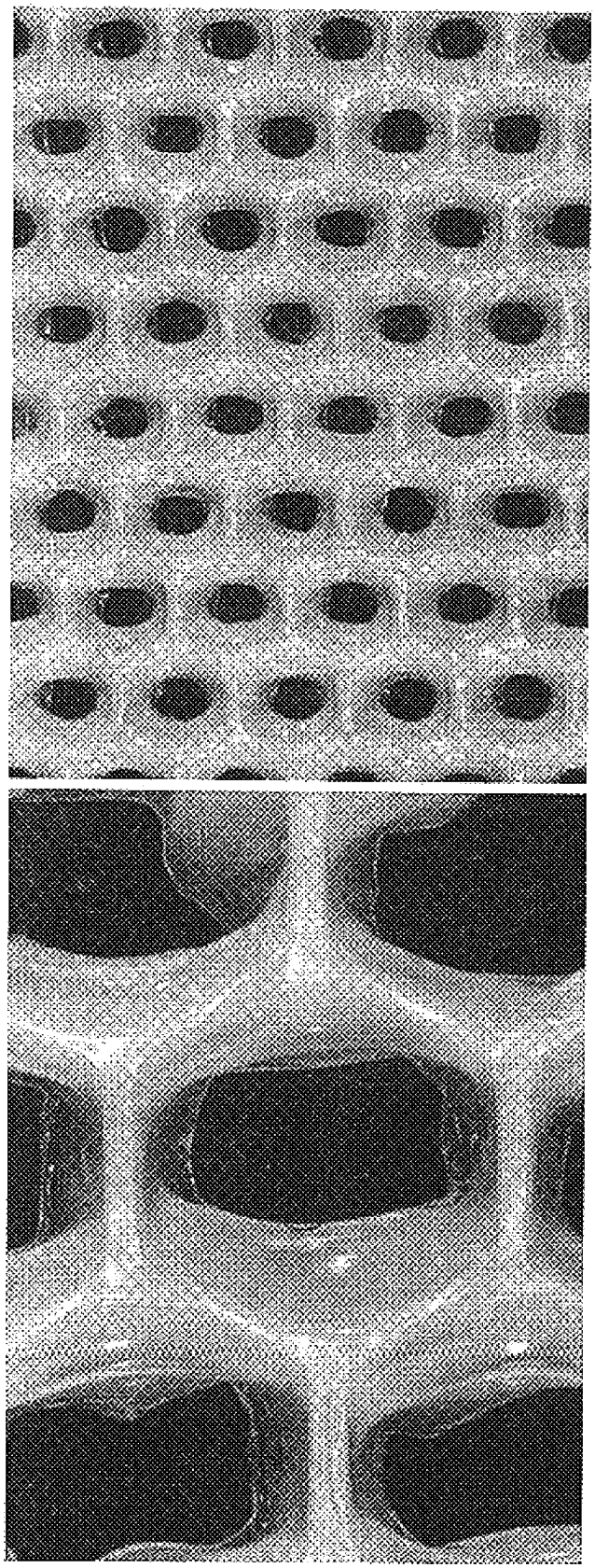
FIG. 19 is a plan view at 50X magnification of Sample 2 and Sample 4 for purposes of comparing the void volume space of the samples.

To further illustrate the substantial increase in void volume space of the films of the invention over existing films, microphotographs of Sample 2 and Sample 4 are set forth in FIGS. 19 and 20. FIGS. 15 and 16 show Samples 2 and 4 at 50X magnification. FIG. 19 shows a plan view of samples 2 and 4. FIG. 20 shows a side cross-sectional view of samples 2 and 4. The substantial increase in void volume space is apparent from each of FIGS. 19 and 20.

Finally, microphotographs of known magnification and scale of dimensions were taken of each of Samples 1–4 to enable empirical calculations of void volume spaces. While the cells of the embodiments described herein are best approximated as a geometric frustum, as taught in Thompson U.S. Pat. No. 4,939,135, it is within the scope of the invention to include other cell shapes such as substantially straight walled cells, as taught in Radel U.S. Pat. No. 4,342,314, and cells which converge to a narrow point and then diverge again toward the apertured end, as taught by Rose U.S. Pat. No. 4,895,749. The resulting geometric calculation for void volume space data for Female Side void volume, Male Side void volume, and the Total Void Volumes are shown below in Table 3.

TABLE 3

| Sample No. | Loft (mils) | Mesh | Cells/m² of film | Female side volume (cc/m²) | Male side volume (cc/m²) | Total Void Volume (cc/m²) |
|---|---|---|---|---|---|---|
| 1 | 20 | 22 | 872,170 | 189 | 339 | 528 |
| 2 | 23 | 25 | 1,090,755 | 247 | 236 | 483 |

TABLE 3-continued

| Sample No. | Loft (mils) | Mesh | Cells/m² of film | Female side volume (cc/m²) | Male side volume (cc/m²) | Total Void Volume (cc/m²) |
|---|---|---|---|---|---|---|
| 3 | 49 | 8.75 | 131,771 | 294 | 752 | 1046 |
| 4 | 51 | 8 | 105,649 | 1357 | 475 | 1832 |

It can be seen from table 3 that the "spill-under" embodiment of applicant's invention, demonstrated by Sample 3 has a substantially greater male side void volume, i.e., 752 cm³, than do any of the other samples. The "spill-over" embodiment of applicant's invention, demonstrated by Sample 4 has a substantially greater female side volume, i.e. 1357 cm³, than do any of the other samples.

In the embodiments shown in FIGS. 13–16, which involve the utilization of channels 278, 396 that are cut below the original plane of the surface of the 8.75 hex (spill under) or honeycomb (spill over) patterns or other patterns not discussed above. The channels 278,396 provide void space or a passageway for fluid flow and direct the fluid flow in preferred directions.

The 8.75 hex spill under pattern, when provided with channels 278, 396, provide an additional spill over volume within the channels 278, 396. The combination of spill-under and channel facilitated spill-over is highly effective, as shown in Table 4 below. Note that the three dimensional apertured film taught by U.S. Pat. No. 4,324,247 to Aziz lacks void volume for facilitating a good distribution of fluid. The film 278 and 396 of this application exhibits improvement of three dimensional apertured film 56 more than a factor of 2 as compared to the high void volume of the 8.75 hex, which provides high void volume for spill-under distribution.

When the same pattern was given channels 278, 396, the film improved by more than double again. Data for Table 4, below, was derived by introducing 5 mL per insult into a weighted chamber 1 inch in diameter by ¾ inch deep. The weight applies ½ pound per square inch pressure over 4" by 4" sample area of three types. The chamber has electrodes that sense the presence of liquid and then absence of liquid. When the electrodes sense the presence and absence of liquid, a timer is stopped and started. ADL material is assembled on top of three layers of absorbent paper in the same 4" by 4" area. The ADL preferably should avoid compression and provide void volume. The Aziz type samples have a 22 mil loft. The standard ADL is of the type described in Table 3, Sample 3. The negative channel ADL type is the standard ADL described above with the addition of channels approximately 15 mil deep, approximately ½" wide and spaced ¼" on centers.

TABLE 4

Repeated Insult ADL Data

| Sample | Insult # | Seconds |
|---|---|---|
| Aziz '247 Type at | 1 | 2.36 |
| 22 mil loft | 2 | 3.86 |
|  | 3 | 4.26 |
| Std. ADL | 1 | 1.45 |
| (described in Table | 2 | 1.75 |
| 3, Sample 3) | 3 | 1.80 |
| Neg. Chnl. ADL | 1 | 0.67 |
| (standard ADL | 2 | 0.80 |
| described above | 3 | 0.80 |

TABLE 4-continued

Repeated Insult ADL Data

| Sample | Insult # | Seconds |
|---|---|---|
| with channels added) | | |

From the above, it will be appreciated that applicant's invention will reduce or eliminate the wetness sensation felt by the user during and after repeated insults as unabsorbed fluid flows from an area of saturated core material to an area of unsaturated core material for absorption. Applicant's invention redirects unabsorbed fluids to non-saturated areas of a core material 16 while preventing substantial contact of the unabsorbed fluids with the topsheet 12. The invention of the applicant prevents an unpleasant feeling of wetness of the topsheet 12 while providing the ability to receive multiple insults at a singular point.

The present invention is illustrated herein by example, and various modifications may be made by a person of ordinary skill in the art. For example, various geometries, materials and multiple-layer film combinations fall within the scope of the invention. As another example, although the present invention has been described in connection with diapers, incontinent articles, sanitary napkins, and related products, the absorbent articles of the present invention are fully applicable to other, similar products, including, without limitation, other body coverings where absorbent materials may be desired. Such body coverings may include medical drapes, medical gowns, medical smocks, ostomy appliances, feminine hygiene products, body transfer sheets, fluid collection pouches, industrial clean room garments and other products.

It is therefore believed that the present invention will be apparent from the foregoing description. While the methods and articles shown or described have been characterized as being preferred it should be obvious that various changes and modifications may be made therefrom without departing from the spirit and scope of the invention as defined in the following claims.

What we claim is:

1. An absorbent article comprising:
    a topsheet;
    an absorbent core; and
    an acquisition distribution layer between said top sheet and said core, wherein said acquisition distribution layer is a three dimensional apertured film having a female side that defines a planar surface and a male side, the male side facing the absorbent core, wherein said acquisition distribution layer defines a total void volume per unit area of greater than 500 cm³/m² within the absorbent article and a male side void volume on the male side of the three dimensional apertured film is greater than 475 cm³/m² and said acquisition distribution layer defines at least one channel distinguishable on said planar surface.

2. The absorbent article according to claim 1 wherein: said channel is continuous.

3. The absorbent article according to claim 1 wherein said channel runs in a direction generally parallel with strands of a polymer that forms the acquisition distribution layer.

4. The absorbent article according to claim 1 wherein: said at least one channel is between approximately 1/32" wide and ¼" wide.

5. The absorbent article according to claim 1 wherein said at least one channel is a plurality of channels; said channels are spaced apart between approximately 1/8" and 1/4" as measured center to center.

6. The absorbent article according to claim 1 wherein: said channel has a depth of less than 1/2 of a loft of said acquisition distribution layer.

7. The absorbent article according to claim 1 wherein: said at least one channel has a depth of approximately 1/3 of a loft of said acquisition distribution layer.

8. The absorbent article according to claim 1 wherein: said topsheet is a vacuum formed film layer.

9. The absorbent article according to claim 1 wherein: said acquisition distribution layer has a plurality of cells wherein adjacent cells each have a hole that allows insult fluids to be rapidly acquired through the acquisition distribution layer.

10. The absorbent article according to claim 9 wherein: said channel places individual ones of said plurality of cells in fluid communication with selected adjacent others of said plurality of cells below said planar surface.

11. The absorbent article according to claim 9 wherein: said plurality of cells have a mesh count of between approximately 2 and 25.

12. The absorbent article according to claim 9 wherein: said plurality of cells have a mesh count of between approximately 4 and 15.

13. The absorbent article according to claim 9 wherein: said plurality of cells have a mesh count of approximately 8.

14. The absorbent article according to claim 9 wherein: said cells have a shape selected from a group comprising hexagonal, circular, oval, elliptical, or polygonal.

15. The absorbent article according to claim 9 wherein: said plurality of cells form a cell pattern that is a combination of at least two shapes selected from a group comprising hexagonal, circular, oval, elliptical, or polygonal.

16. The absorbent article according to claim 1 wherein said total void volume per unit area is greater than 1000 $cm^3/m^2$.

17. The absorbent article according to claim 1 wherein said total void volume per unit area is greater than 750 $cm^3/m^2$.

18. An absorbent article according comprising:

a top sheet;

an absorbent core;

a channeled acquisition distribution layer between said top sheet and said absorbent core, wherein said acquisition distribution layer is a three dimensional apertured film having a female side and a male side, the male side facing the absorbent core, and a total void volume per unit area of at least 500 $cm^3/m^2$ within the absorbent article, and a male side void volume on the male side of the three dimensional apertured film is greater than 475 $cm^3/m^2$.

19. The absorbent article according to claim 18 wherein: said female side defines a planar surface; and said channels are formed below said planar surface.

* * * * *